(12) United States Patent
Kloog et al.

(10) Patent No.: US 6,462,086 B1
(45) Date of Patent: Oct. 8, 2002

(54) NON-MALIGNANT DISEASE TREATMENT WITH RAS ANTAGONISTS

(75) Inventors: Yoel Kloog, Herzliya (IL); Joab Chapman, Kiryat Ono (IL); Dimitrius Karussis, Jerusalem (IL); Rafael Bruck, Rishon Le-Zion (IL); Shimon Reif, Karney Shomron (IL); Michael Brownstein, Rockville, MD (US)

(73) Assignee: Ramot University Authority for Applied Research and Industrial Development Ltd. (IL)

( * ) Notice: Subject to any disclaimer, the term of this patent is extended or adjusted under 35 U.S.C. 154(b) by 0 days.

(21) Appl. No.: 09/597,332

(22) Filed: Jun. 19, 2000

Related U.S. Application Data

(60) Provisional application No. 60/140,192, filed on Jun. 18, 1999.

(51) Int. Cl.$^7$ .......................... A01N 37/10; A01N 43/40

(52) U.S. Cl. .................. 514/568; 514/345; 514/350

(58) Field of Search ................................ 514/333, 568, 514/345, 350

(56) References Cited

U.S. PATENT DOCUMENTS

| | | | |
|---|---|---|---|
| 5,580,955 A | 12/1996 | Nur-E-Kamal et al. | ..... 530/324 |
| 5,705,528 A | 1/1998 | Kloog | ......................... 514/524 |

FOREIGN PATENT DOCUMENTS

| | | | | |
|---|---|---|---|---|
| WO | WO-97/30992 | * | 8/1997 | ................. 514/221 |
| WO | WO-98/02436 | * | 1/1998 | ................. 514/221 |
| WO | WO-99/18951 | * | 4/1999 | ................. 514/221 |

OTHER PUBLICATIONS

Charles Z. Ding et al, "Imidazole–Containing Benzodiazepines and Analogs as Inhibitors of Farnesyl Protein Transferase", WO–97/30992, Aug. 1997, CA 127:278213 (abstract).*
Ohtsuka, et al., Biochim. Biophys. Acta. 1310:223–232 (1996).
V. Taneja, et al., J. Clin. Invest. 101:921–926 (1998).
Gana–Weisz, et al., Biochem. Biophys. Res. Commun. 1997, 239:900–904.
Marciano, et al., Bioerg. Med. Chem. Lett. 1997, 7:1709–1714.
Paterson 1978 Immunological Diseases, 3rd Ed. 1400 Little, Brown and Company, Boston.
Lieder, et al. 1988 Science 239:181.
Varela, et al., 1991 Immunol. Today 12:159.
Cohen, et al., Immunol. Today 12:105 (1991).
Lehmann, et al., 1997 Clin Immunol Immunopathol 85:202.
Aharonson, et al., Biochim. Biophys. Acta 1406:40–50 (1998).
Baldari, et al., 1993, J. Biol. Chem. 268:2693.
Siegel, et al., 1991, Semin Immunol. 3:325.
Boguski, et al., 1993, Nature 366:643.
Cox, et al., 1997, Biochim. Biophys. Acta 1333:F51.
Marshall, 1996, Curr. Opin. Cell Biol. 8:197.
Scheffzek, et al., 1997 Science 277:333.
Kloog, et al., Exp. Opin. Invest. Drugs 8(12):2121–2140.
Marciano, et al., 1995, J. Med. Chem. 38, 1267–72.
Haklai, et al., 1998 Biochemistry 37, 1306–1314.
Casey, et al., Proc. Natl. Acad. Sci. USA 86, 8323.
Hancock, et al., 1989, Cell 57, 1167.
Aharonson, et al., 1998, Biochim. Biophys. Acta. 1406, 40–50.
Martin, et al., 1995, Crit Rev Clin Lab Sci 32:121.
Raine, 1994, Ann Neurol 36 (suppl.):S61.
Hafler, et al., 1989, Immunol Today 10:104.
Lublin, 1985, Springer Semin Immunopathol 8:197.
van der Veen, et al., 1989, J Neuroimmunol. 21:183.
Karussis, et al., 1998, J. Neurol Sci 153:239.
Dalakas, 1995 Ann Neurol 37 Suppl 1:S2.
Lisak, 1988, Neurology.
Karussis, et al., 1992, J. Immunol. 148:1693.
Diebler, et al., 1972 Prep. Biochem. 2:139.
Barany, et al., 1980, Academic Press, NY 2:1.
Bernard, et al., 1975, J Immunol 114:1537.
Haklai, et al., 1998, Biochemistry 37:1306.
Niv, et al., 1999, J Biol Chem 274:1606–1613.
Padula, et al., 1991, J Immunol 146:879.
Kuchroo, et al., 1992, J Immunol 148:3776.
Kaladlubowski, et al., Brain Res 1980, 184:439–454.
Shin, et al., Biochim. Biophys. Res. Commun. 1996, 224:5–9.
Marom, et al., 1995, J. Biol Chem., 270:22263–22270.
Allen, C.F.H. and McKay, Org. Synthesis 11:580.
Hann, et al., 1988, Lab Invest 59:115–125.
Cliffer, et al., 1998, Muscle Nerve 21:1405–1413.
Shoenfeld, et al., 1984, N Engl J Med 311:1019–29.
Shoenfeld, et al., Immunol Today 1989, 10:123–6.
Ballow, et al., JAMA 1997, 278:2008–17.
Gharavi, et al., Haemostatis 1994, 24:204–7.
Shoenfeld, Curr. Opin. Rheumatol 1989, 1:360–8.

(List continued on next page.)

Primary Examiner—Paul J. Killos
(74) Attorney, Agent, or Firm—Lerner, David, Littenberg, Krumholz & Mentlik, LLP

(57) ABSTRACT

Disclosed is a method for inhibiting Ras-induced or mediated proliferation of cells associated with a non-malignant disease, disorder or pathological condition. The method entails administering to a patient a Ras antagonist in an amount effective to inhibit the proliferation. The invention is particularly applicable to diseases characterized by a proliferation of T-cells such as autoimmune disease, e.g., type 1 diabetes, lupus and multiple sclerosis, and pathological states such as graft rejection induced by the presentation of a foreign antigen such as a graft in response to a disease condition (e.g., kidney failure). Other non-malignant diseases characterized by proliferations of cells include cirrhosis of the liver and restenosis. Preferred Ras antagonists are S-trans-trans farnesylthiosalicylic acid (FTS) and structurally related compounds (or analogs) thereof.

22 Claims, 17 Drawing Sheets

OTHER PUBLICATIONS

Brey, et al., Ann NY Acad Sci 1997, 823:97–106.
Mendlovic, et al., 1988 Proc Natl Acad Sci USA 85:2260–4.
Schoenfeld, Isr J Med Sci 1994 30:10–8.
Krause, et al., Int Arch Allergy Immunol 1996, 111:355–61.
Blank, et al., J Autoimmun 1994, 7:441–55.
Gharavi, et al. , J. Clin Invest 1992, 90:1105–9.
Garcia, et al., Am J Reprod Immunol 1997, 37:118–24.
Blank, et al., 1990 Clin Immunol Immunopathol 54:87–97.
George, et al., Circulation 1998, 97:900–6.
Brey, et al., Lupus, 1997, 6:645–51.
Cameron, et al., Immunology, 1986, 59:187–93.
Dziarski, J Clin Lab Immunol 1985, 16:93–109.
Bernstein, et al., Clin Exp Immunol 1993, 93:418–23.
Kiberd, et al., J Lab Clin Med 1994, 124:496–506.
Woo, et al., Clin Exp Immunol 1995, 100:118–25.
Warner, et al., Arthritis Rheum 1994, 37:289–97.
Hendrickson, et al., Arthritis Rheum 1994, 37:587–94.
Merino, et al., J. Autoimmun 1995, 8:33–45.
Hori, et al., Dig Dis Sci 1993, 38:2195–202.
Woessner, Arch Biochem Biophys 1961, 93:440–447.
Pinzani, et al., J Clin Invest 1989 84:1786–1793.
Marra, et al., Gastroenterology 1997 112:1297–1306.
Carloni, et al., Gastroenterology 1996 110:1127–1136.
Schuppan, et al., Cellular and Molecular Aspects of Cirrhosis, Paris: John Libbey Eurotext, Les Editions INSERM 1992 216:115–34.
Clement, et al., Molecular and Cell Biology of Liver Fibrogenesis, Dordre: Kluwer Academic Publishers 1992, 85–98.
Ogawa, et al., Am J Pathol 1986 125:611–619.
Dashti, et al., Eur Surg Res 1989 21:83–91.
Chieli, et al., Toxicology 1984 31:41–52.
Liu, et al., Circulation 79:1374–1387 (1989).
Fuster, et al., N. Engl. J Med. 236:242–250 (1992).
Libby, et al., Circulation 86 (Suppl.) III47–III52 (1992).
Ross, Nature (Lond.), 362:801–809 (1993).
Hanke, et al., Circulation Res. 67:651–659 (1990).
Shi, et al., Circulation 94: 1655–1664 (1996).
Andersen, Circulation 93:1716–1724 (1996).
Ridker, et al., Engl. J. Med. 336:973–979 (1997).
Ridker, et al., Circulation 98:731–733 (1998).
Koeing, Eur. Heart J. Suppl.1:T19–T26 (1999).
Clowes, et al., Lab Invest. 49:327–334 (1983).
Kaltenbach, et al., Eur. Heart J. 6:276–281 (1985).
Nobuyoshi, et al., J. Am. Coll. Cardiol. 12:616–623 (1988).
Rita Trial Participants (1993) Lancet. 341:573–580.
Califf, et al., J. Am. Coll. Cardiol. 17:2B–13B (1991).
Popma, et al., Circulation 84:1426–1436 (1991).
Franklin, et al., Coronary Artery Dis. 4:232–242 (1993).
Teirstein, et al., N. Eng. J. Med 336:1697–1703 (1997).
Condado, et al., Circulation 96:727–732 (1997).
Katz, et al., JOC 18:1380–1402 (1953).
Allen, et al., Org. Synthesis IV:295.
Okachi, et al., J. Med Chem. 28:1772–1779 (1985).
Carmelin, et al., J. Med Chem 29:743–751 (1994).
Tarbell, et al., Am. Soc. 74:48 (1952).
Tarbell, et al., Org. React. 5:193–228 (1949).
Muller, et al., Exp Pathol 1988 34:229–36.
Pinzani, et al., J Clin Invest 1992 90:642–646.
Casini, et al., Gastroenterology 1993 105:245–253.

* cited by examiner

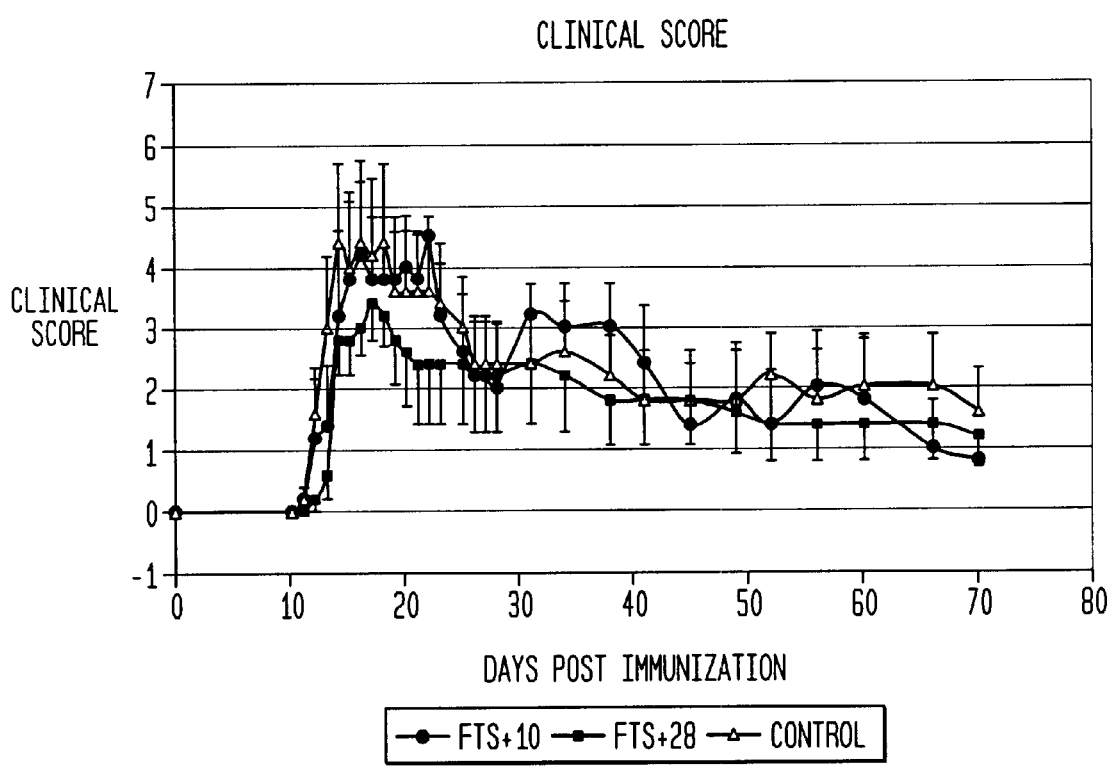

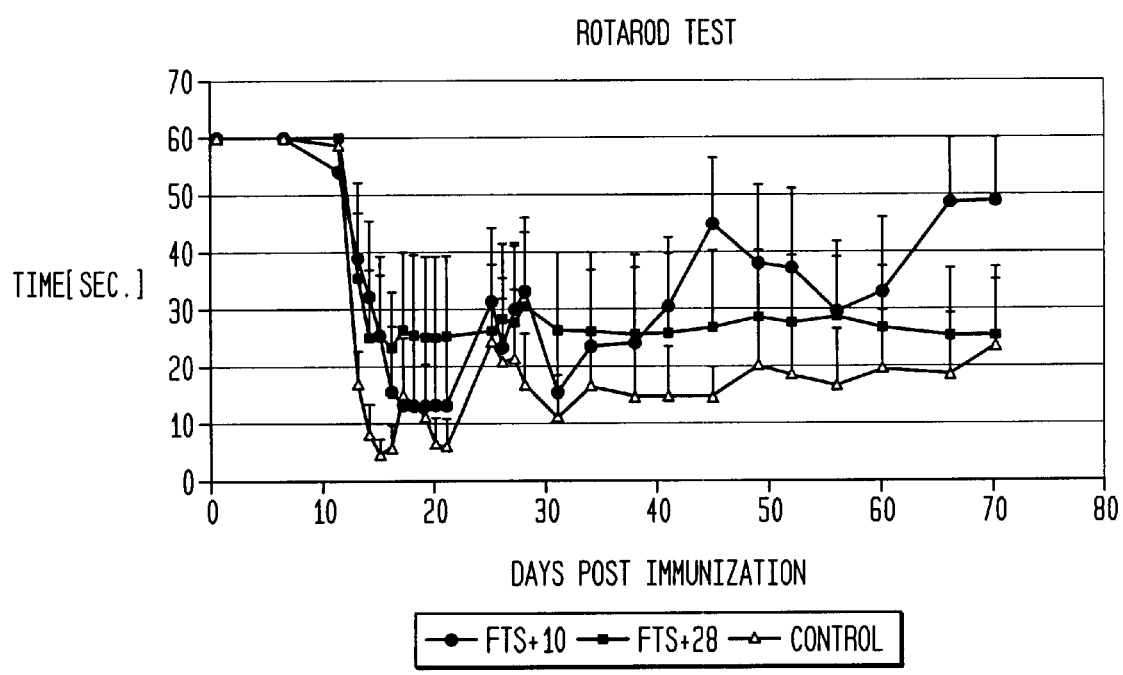

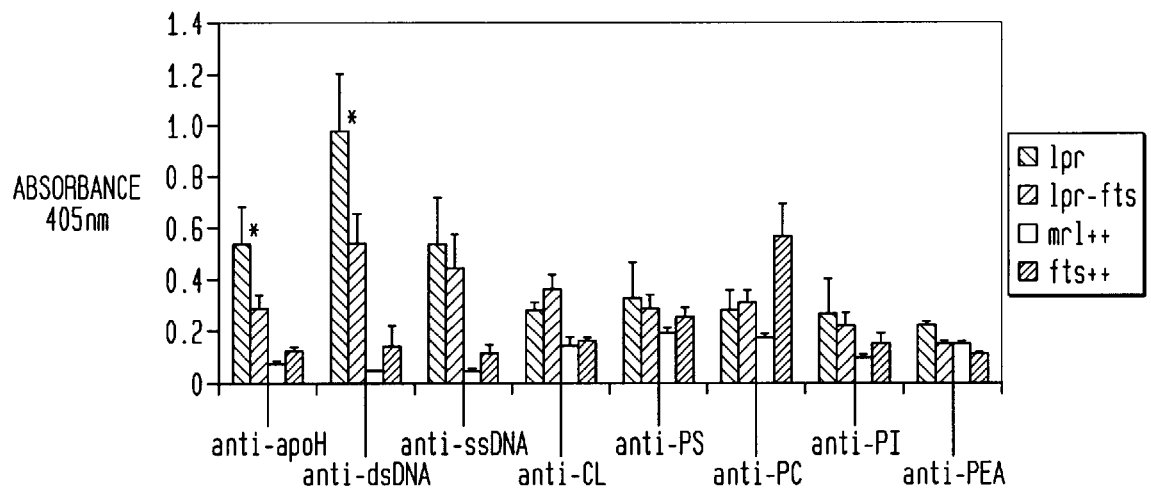
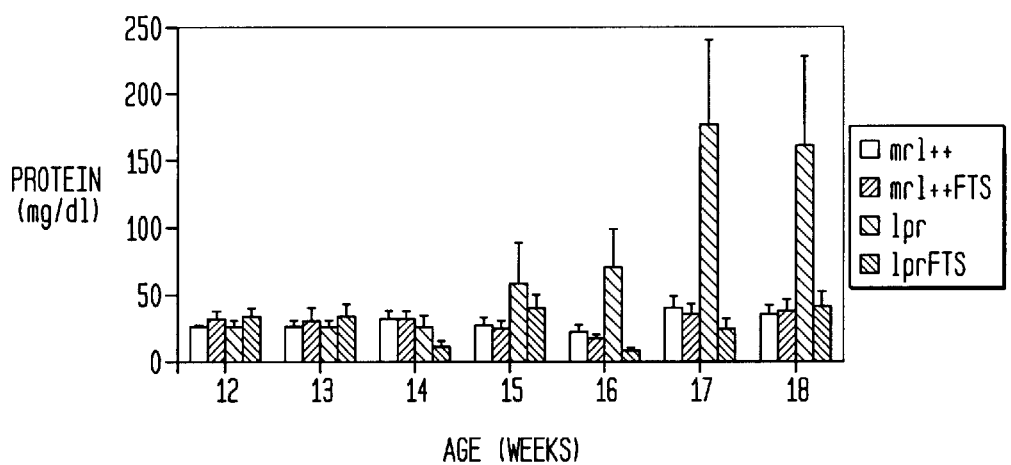

FTS TREATMENT

CONTROL TREATMENT

US 6,462,086 B1

NON-MALIGNANT DISEASE TREATMENT WITH RAS ANTAGONISTS

CROSS-REFERENCE TO RELATED APPLICATIONS

This application claims priority under 35 U.S.C. §119(e) from U.S. application Ser. No. 60/140,192, filed Jun. 18, 1999.

FIELD OF THE INVENTION

The present invention relates to the inhibition of the onset of or the treatment of non-malignant diseases, and particularly diseases having pathologies involving Ras-induced proliferation of cells.

BACKGROUND OF THE INVENTION

Autoimmune diseases include disorders involving dysfunction of the immune system, which mediates tissue damage. Any organ may be affected by such processes through precipitation of immune complexes, cellular immunity, or inappropriate generation or action of immunohormones such as cytokines. Epidemiologically, autoimmune diseases are significant because of the numbers of patients that they affect and the serious morbidity and mortality that they cause. Common chronic systemic diseases in this group include diabetes mellitus, thyroid disease, rheumatoid arthritis, systemic lupus erythematosus (SLE), primary antiphospholipid syndrome (APS), and a variety of diseases that affect the central nervous system. Neurological autoimmune diseases include disorders specific to the nervous system such as myasthenia gravis, Lambert Eaton myasthenic syndrome, Guillain-Barre syndrome, polymyositis, and multiple sclerosis. In addition, there are neurological complications of the systemic autoimmune diseases. Factors predisposing to autoimmune diseases include genetic predisposition and environmental agents such as certain infections and pharmaceutical products. Such factors result in pathological activation of the immune response in susceptible individuals, which is generally controlled by T lymphocytes (T cells). The activation T cells and B subtypes, involves a complex interaction of cell surface receptors resulting in equally complex signal transduction pathways which eventually affect gene regulation. Full activation of lymphocytes requires parallel stimulation of several signal transduction pathways. See Ohtsuka, et al., Biochim. Biophys. Acta. 1310:223–232 (1996).

Although there is growing understanding about the function of T cells in the immune response, this knowledge has not explained the basis of most autoimmune diseases. There are still questions to be resolved such as how tolerance to self in normal individuals is maintained; how tolerance is broken in autoimmunity; and which autoantigens trigger the immune system to produce specific diseases. A recent review by V. Taneja and C. S. David (J. Clin. Invest. 101:921–926 (1998)) provides an overview of important issues in this field and emphasized how the generation of transgenic mice expressing functional HLA molecules is important for understanding the function of certain molecules in the induction of autoimmune disease, as well as circumvention of the xenogenic barrier. Regardless of the mechanisms involved in induction of autoimmune disease or the rejection of grafts, the common pathway for these events includes activation of a relatively small number of T lymphocytes.

Several immunosuppressive and immunomodulating treatments have been tested and subsequently applied in the treatment of autoimmune diseases. Gana-Weisz, M., HaMai, R., Marciano, D., Egozi, Y., Ben-Baruch, G., and Kloog, Y. The Ras antagonist S-farnesylthiosalicylic acid induces inhibition of MAPK activation. Biochem. Biophys. Res. Commun. 1997; 239: 900–904; Marciano, D., Aharonson*, Varsano, T., Haklai, R., and KO, Y. Novel inhibitors of the prenylated protein methyltransferase reveal distinctive structural requirements. Bioerg. Med. Chem. Lett. 1997; 7, 1709–1714; Paterson P. Y. (1978) The demyelinating diseases: clinical and experimental studies in animals and man. In: Immunological Diseases, 3rd Edition, (ed. by M. Smater, N. Alexander, B. Rose, W. B. Sherman, D. W. Talmage and J. H. Vaughn) p. 1400. Little, Brown and Company, Boston.

The main drawback of immunosuppressive modalities is that the induction of generalized suppression of all T-cells and immune functions is associated with long-term and cumulative side effects. In addition, it is now believed that broad suppression of immune cells may also cancel or neutralize the potential beneficial effects of down-regulatory cells such as suppressors and suppresor inducers or cytokines such as IL-10, on the autoimmune lymphocytes. Karussis, et al., supra; Gana-Weisz, et al., supra, Lieder, O., T. Reshef, E. Berauud, A. Ben-Nun, and I. R. Cohen. 1988, Anti-idiotypic network induced by T cell vaccination against experimental autoimmune encephalomyelitis, Science 239:181; Varela, F. J., and A. Coutinho, 1991, Second generation immune networks, Immunol. Today 12:159; Cohen, I. R., and D. B. Young. 1991, Autoimmunity, microbial immunity and the immunological homunculus, Immunol. Today 12:105; Lehmann, D., D. Karussis, R. Mizrachi-Koll, A. S. Linde, and O. Abramsky, 1997, Inhibition of the progression of multiple sclerosis by linomide is associated with upregulation of CD4+/CD45RA+ cells and downregulation of CD4+/CD45RO+ cells, Clin Immunol Immunopathol 85:202.

Therefore, current approaches for the treatment of autoimmune diseases advocate the use of immunomodulators or specific immunosuppressing medications. The goal of such research is specific suppression of only the lymphocytes with the autoimmune potential. The search for such specific suppressors is a formidable challenge, particularly considering the complex networks of signal transduction pathways associated with lymphocyte growth and differentiation, where many such pathways are common to all lymphoid lineages and to other cells.

In addition to autoimmune disease, there are several other diseases in which proliferation of normal cells other than T-cells constitutes part of the pathology.

SUMMARY OF THE INVENTION

An aspect of the present invention is directed to a method for inhibiting Ras-induced proliferation of cells associated with a non-malignant disease, disorder or pathological condition. The method entails administering to a patient (a human or other mammal) a Ras antagonist in an amount effective to inhibit the proliferation. The invention is particularly directed to autoimmune diseases characterized by a proliferation of T-cells (e.g., normal T-cells) such as type 1 diabetes, lupus and multiple sclerosis. A non-autoimmune disorder that involves proliferations of T-cells is graft rejection. Other diseases include cirrhosis of the liver, post-angioplasty and restenosis and graft rejection.

Another aspect of the present invention is directed to a method of inhibiting Ras-mediated proliferation of cells associated with a non-malignant disease, pathological state or disorder (collectively "disease"), comprising contacting the cells with a Ras antagonist in an amount effective to inhibit the proliferation.

The proliferation, hypertrophy or overgrowth of cells that is common to these diseases is mediated by Ras. This protein becomes activated by a series of biochemical events after it binds or docks to a particular site on the inner surface of the cell membrane. The activation of Ras then leads to another series of inter-related biochemical reactions or signal transduction cascades that ultimately produce cell growth and division. The Ras antagonists of the present invention affect (e.g., inhibit) the binding of Ras to the cell membrane, which in turn reduces or inhibits the unwanted cell proliferation.

Preferred Ras antagonists include farnesyl thiosalicylic acid (FTS) and structurally related compounds or analogs thereof, which are believed to function by displacing or dislodging Ras from its membrane anchor. These organic compounds may be administered parenterally or orally. In a particularly preferred embodiment, the Ras antagonist is formulated for oral or parenteral administration by complexation with cyclodextrin.

FTS has been shown to affect the growth of cancers in animals mediated by oncogenic forms of Ras, including melanomas and lung, colon, pancreatic, uterine and Merkel cell cancers. The results of these experiments showed that FTS achieved greater than 90% reduction in cancer cell growth in some cases without significant toxic effects associated with standard cancer chemotherapy. The results also showed that similar dosages of FTS used in cancer treatment had very little, if any, effect on normal cells. See Aharonson, et al., Biochim. Biophys. Acta 1406:40–50 (1998). It was known that the proliferation of normal cells associated with various non-malignant diseases (e.g., T-cells associated with various autoimmune diseases, stellate cells associated with cirrhosis and smooth muscle cells associated with post angioplasty restenosis) was mediated at least in part by normal or non-oncogenic Ras. Still, it was not expected that FTS and similarly active compounds could be used to achieve a therapeutic benefit in patients afflicted with diseases characterized by proliferations of normal cells.

The methods of the present invention offer several advantages over current immunosuppressive and immunomodulatory treatment modalities. They are generally non-cytotoxic to all dividing cells, non-toxic at therapeutically effective doses, and do not result in general immunosuppression.

BRIEF DESCRIPTION OF THE FIGURES

FIGS. 4A and 4B are graphs illustrating clincial score and mean time respectively, on a rotating bar (rotarod) in EAN rats treated with FTS for 10 (FTS+10) or 28 (FTS+28) days or with sham carrier (control);

FIGS. 12A and 12B are graphs illustrating grip strength in saline-treated MRL/lpr mice, FTS-treated MRL/lpr mice, saline-treated MRL/++ mice and FTS-treated MRL/++ mice, wherein FIG. 12A illustrates mean ±SE values for performance of saline-treated (circles) and FTS-treated (squares) MRL/lpr mice at 12–17 weeks of age, and FIG. 12B illustrates mean ±SE values for performance of 4 groups at weeks 15–17 (MRL/lpr mice (n=25), FTS-treated MRL/lpr mice (n=25), saline-treated MRL/++ mice (n=20) and FTS-treated MRL/++ mice (n=15));

FIGS. 13A and 13B are bar graphs illustrating performance in an open field of MRL/lpr mice (saline and FTS-treated) and saline-treated MRL/++ mice during 20 minutes, wherein FIG. 13A illustrates total distance covered and FIG. 13B illustrates time spent in the center of the open field of the three groups measured as mean±SE values for 5 mice in each group;

FIG. 14 is a bar graph that illustrates levels of various autoantibodies in 14 MRL/lpr mice treated with FTS and 14 controls, measured in terms of absorbance at 405 nm, wherein the standard error bars denote standard deviations;

FIG. 15 is a bar graph illustrating Mean±SE levels in urine from MRL/++ (mrl++) and MRL/lpr (lpr) mice (10 per group) treated with vehicle alone and with FTS (FTS) at the indicated ages;

DETAILED DESCRIPTION OF THE INVENTION

Figure 1:
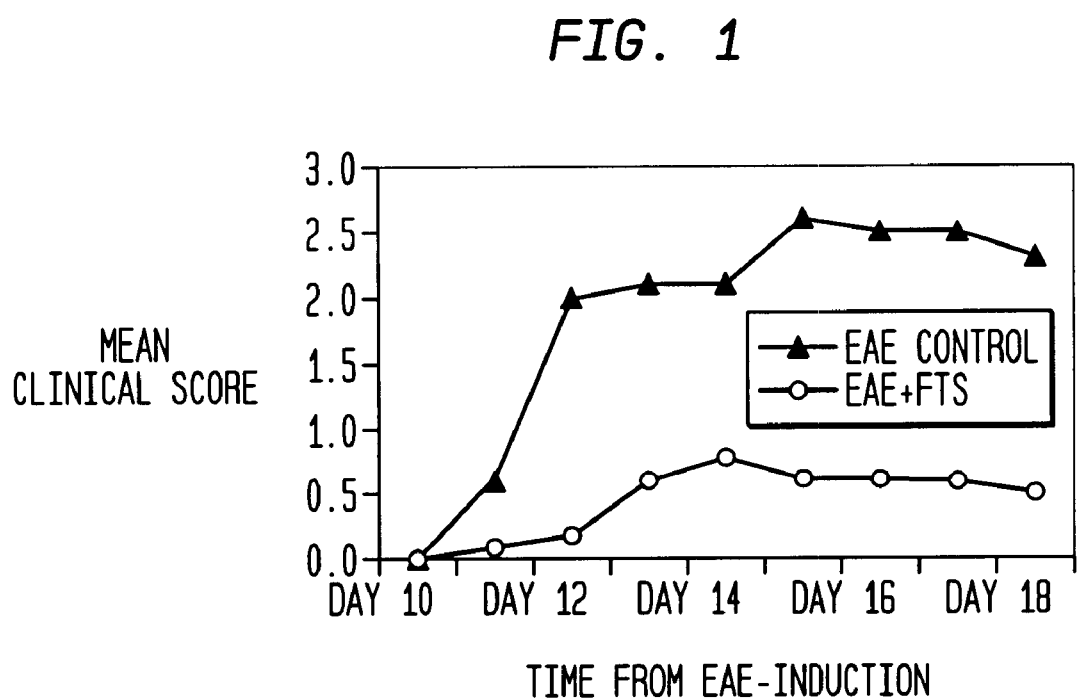
FIG. 1 is a graph that illustrates the clinical course of acute EAE treated by FTS in terms of mean clinical scores per group daily wherein the severity of the disease was graded according to a 0–6 scale.

The methods of the present invention are directed to the treatment of non-malignant diseases, pathological states or other disorders that feature or otherwise include Ras-induced proliferation of cells. The etiology of the one such category of diseases is initiated by tissue injury or damage which induces the release of one or more growth factors and that then induces Ras-mediated hypertrophy or overgrowth of normal cells. Examples include cirrhosis of the liver, which involves proliferation of normal hepatocytes, stellate cells and connective tissue cells. Another example is post-angioplasty restenosis. Here, the insertion of an intra-arterial stent causes damage, release of growth factors and proliferation of normal smooth muscle cells. Autoimmune diseases characterized by an overgrowth of normal T-cells in response to presentation of an autoantigen through a T-cell receptor, constitute a second category of disease. Diseases in this category include systemic lupus erythmatosus (SLE), multiple sclerosis (MS), antiphospholipid syndrome (APS), psoriasis, type 1 (i.e., autoimmune) diabetes and rheumatoid arthritis. Graft rejection is a non-autoimmune disorder that involves a proliferation of T cells, in response to the presentation of a foreign antigen (i.e., the graft). Thus, the targeted cells are normal in the sense that they are non-malignant and functioning normally but in response to a stimulus such that the overall effect contributes to the disease pathology.

The activation of T lymphocytes involves a complex interaction of cell surface receptors resulting in the activation of equally complex signal transduction pathways, which eventually affect gene regulation. See, Baldari, et al., 1993, J. Biol. Chem. 268, 2693; Siegel, et al., 1991, Semin Immunol. 3,325. Full activation of lymphocytes requires stimulation in parallel of different signal transduction pathways (Siegel, supra.) including two prominent pathways, the one of which involves the src-like tyrosine kinase lck, the GTP-binding protein Ras and the MAPK cascade, while the other involves the ZAP-70 tyrosine kinase, PLCγ and calcium influx (Ohtsuka, et al., 1996, Biochim. Biophys. Acta 1310, 223). Receptor mediated activation of the Ras-pathways involves recruitment of adaptor proteins and guanine nucleotide exchange factors (GEFs) to distinctive domains in the cell membrane where the Ras GEF (SOS) induces the exchange of GDP for GTP on Ras and thus activates this GTP binding protein. See, Boguski, et al., 1993, Nature 366, 643; Cox, et al., 1997, Biochim. Biophys. Acta 1333, F51; Marshall, 1996, Curr. Opin. Cell Biol. 8, 197 and Scheffzek, et al., 1997, Science 277, 333. The activation of Ras and its dependent pathways MAPR cascade are major, absolutely necessary, biochemical events during lymphocyte activation and proliferation leading to induction of immediate early genes such as the IL-2 receptor gene.

Ras protein is the on/off switch between hormone/growth factor receptors and the regulatory cascading that result in cell division. For Ras to be activated (i.e., turned on) to stimulate the regulatory cascades, it must first be attached to the inside of the cell membrane. Ras antagonist drug development aimed at blocking the action of Ras on the regulatory cascades has focused on interrupting the association of Ras with the cell membrane, blocking activation of Ras or inhibiting activated Ras. The details of the approaches to development of Ras antagonists are reviewed in Kloog, et al., Exp. Opin. Invest. Drugs 8(12):2121–2140 (1999). Thus, by the term "ras antagonist", it is meant any compound or agent that targets one or more of these phenomena so as to result in inhibition of cell proliferation.

In one embodiment, the Ras antagonist is represented by formula I:

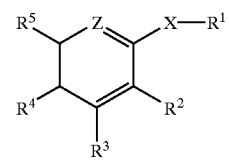

wherein $R^1$ represents farnesyl, geranyl or geranyl-geranyl;

Z represents C—$R^6$ or N;

$R^2$ represents H, CN, the groups $COOR^7$, $SO_3R^7$, $CONR^7R^8$, COOM, $SO_3M$ and $SO_2NR^7R^8$, wherein $R^7$ and $R^8$ are each independently hydrogen, alkyl or alkenyl, and wherein M is a cation;

$R^3$, $R^4$, $R^5$ and $R^6$ are each independently hydrogen, carboxyl, alkyl, alkenyl, aminoalkyl, nitroalkyl, nitro, halo, amino, mono- or di-alkylamino, mercapto, mercaptoalkyl, axido, or thiocyanato;

X represents O, S, SO, $SO_2$, NH or Se; and the quaternary ammonium salts and N-oxides of the compounds of formula (I) wherein Z is N.

These compounds represent farnesyl-thiosalicylic acid (FTS) (e.g., S-trans, trans-FTS) and its analogs. In embodiments wherein $R^2$ represents H, $R^3$ is preferably a carboxyl group. The structures of FTS and two preferred analogs are as follows:

(i) FTS:

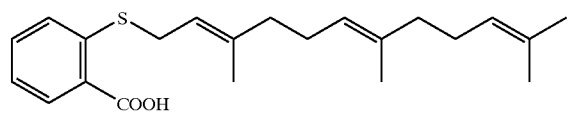

(ii) 2-chloro-5-farnesylaminobenzoic acid (NFCB):

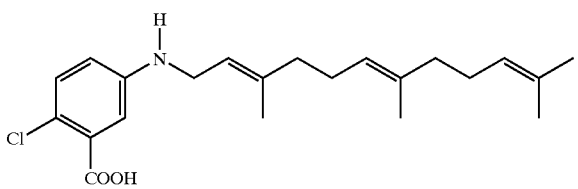

(iii) farnesyl thionicoatinic acid (FTN):

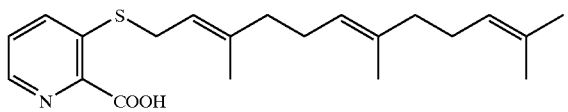

These compounds are the subject of U.S. Pat. No. 5,705,528. Methods of synthesizing the compounds are also disclosed therein.

Yet other FTS analogs embraced by formula I include 5-fluoro-FTS, 5-chloro-FTS, 4-chloro-FTS and S-farnesyl-methylthiosalicylic acid (FMTS). Structures of these compounds are set forth below.

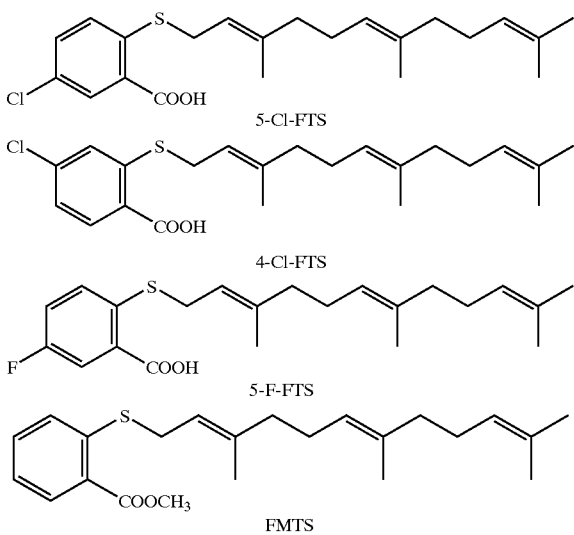

Methods for synthesizing these compounds are described in Example 7. Compounds useful in the present invention are further disclosed in Marciano, et al., 1995, J. Med. Chem. 38, 1267; Haklai, et al., 1998, Biochemistry 37, 1306; Casey, et al., Proc. Natl. Acad. Sci. USA 86, 8323; Hancock, et al., 1989, Cell 57, 1167 and Aharonson, et al., 1998, Biochim. Biophys. Acta. 1406, 40.

A particularly preferred agent is FTS. This compound destabilizes the proper attachment of Ras to the cell membrane which is promoted by the Ras carboxy terminal S-farnesyl cysteine required for Ras signaling. The unique properties of FTS among other compounds that of the present invention mimic Ras anchorage moieties confer on it the ability to disrupt the interactions of Ras with the cell membrane in living cells without cytotoxicity. Without intending to be bound by any particular theory of operation, it is believed that its mechanism of action involves a dual effect on membrane Ras where initially (within 30 min) FTS releases Ras from constraints on its lateral mobility which is followed by release of Ras into the cytoplasm and then by Ras degradation. The reduced amount of Ras and the altered membrane mobility of Ras in FTS-treated fibroblasts and human tumor cells are then manifested in the inhibition of Ras mediated signaling to the mitogen activated protein kinase (MAPK) Erk. This is also believed to explain why FTS inhibits proliferation of Ras-transformed cells and inhibits the mitogenic stimuli of T-cell antigens and of growth factors such as thrombin and EGF, PDGF and FGF.

Other Ras antagonists useful in the present invention may be identified by using the cell free membrane assays and cellular assays described in WO 98/38509. This patent publication describes several assay systems designed to determine the ability of a candidate agent to dislodge activated Ras from its membrane. In general, the assay material that contains specific membranes having a known and detectable quantity of Ras anchored thereto is exposed to the candidate agent. The assay material is then separated into a membrane fraction containing the membranes and a cytosolic fraction of a balance of the material remaining after the specific membranes are removed. A fraction of the known quantity of the labeled Ras contained in the membrane and cytosolic fraction is determined as a measure of the ability of the candidate agent to disrupt membrane association of Ras. A particularly convenient source of activated Ras-anchored membranes is membranes isolated from Ras transformed cancer cells such as Panc-1 cells. The ras remaining in the memberances after exposure to a candidate agent can be measured by standard immunoassays using anti-Ras antibodies.

In general, the Ras antagonists or agents of the present invention are substantially insoluble in water and saline solutions such as PBS Thus, in one embodiment, the agents are salified [e.g., an $NA^+$, $K^+$ or $NH^+$ form] and formulated with an organic solvent such an alkyl gallates and butylated hydroxyanisole containing lecithin and/or citric acid or phosphoric acid. In these formulations, the alkyl gallate, etc., is present in an amount of from 0.02% to about 0.05%, and the citric or phosphoric acid is present in an amount of about 0.01%. These formulations are suitable for parenteral administraiton.

In addition to being insoluble in water, various Ras antagonists such as FTS and its analogs are not active when administered orally. In one embodiment of the present invention, both of these shortcomings are overcome by formulating the agent in cyclodextrin. This technology is the subject of U.S. Pat. Nos. 5,681,828 and 5,935,941. Cyclodextrins are a group of compounds consisting of, or derived from, the three parent cyclodextrins—alpha-, beta- and gamma-cyclodextrins. Alpha-, beta- and gamma-cyclodextrins are simple oligosaccharides consisting of six, seven or eight anhydroglucose residues, respectively, connected to macrocyles by alpha (1 to 4) glycosidic bonds. Each of the glucose residues of a cyclodextrin contains one primary (O6) and two secondary hydroxyls (O2 and O3) which can be substituted, for example, methylated. Many cyclodextrin preparations in practical use are mixtures of chemically individual derivatives in which only a part of hydroxy groups were substituted and which differ in number and position of these substituents.

Cyclodextrins solubilize insoluble compounds into polar media by forming what is known as an inclusion complex between the cyclodextrin and the insoluble compound; cyclodextrin solubilization power is directly proportional to the stability of the complex. Inclusion complexes are non-covalent associations of molecules in which a molecule of one compound, called the host, has a cavity in which a molecule of another compound, called a guest is included.

Derivatives of cyclodextrins are used as the hosts, and the insoluble compound is the guest.

In this invention, many different cyclodextrin derivatives may be used. These include several types of mixtures of partially methylated cyclodextrins. One type is a commercial preparation (Wacker Chemie, Beta W7M1.8) in which the methyl groups are about equally distributed between the primary and secondary hydroxyls of glucopyranose residues; it is abbreviated as RAMEB. A second type has methyls predominantly on the secondary hydroxyls. These derivatives are described in U.S. Pat. No. 5,681,828. A third type of methylated cyclodextrins is formed by those cyclodextrin derivatives or their mixtures that have more than half of their secondary hydroxy groups (i.e., O2 and O3) methylated Other mixtures of cyclodextrin derivates are partial 2-hydroxypropyl ethers, abbreviated as HPACD, HPBCD or HPGCD for derivatives of alpha-, beta- and gamma-cyclodextrins, respectively.

To potentiate the formation of inclusion complexes between the cyclodextrins and the Ras antagonists, highly methylated cyclodextrins may be covalently or non-covalently complexed with less substituted cyclodextrins.

Briefly, the Ras antagonist is salified and dissolved in an appropriate solvent, and then added to a solution of metholated cyclodextrin in PBS. The result of the solution is sterilized and then the solvent is removed. To prepare a formulation suitable for oral administration, the resultant cyclodextrin/FTS complex is mixed with a suitable binder and then pressed into buccal tablets. These tablets dissolve when held in the mouth against the mucus membrane. It is believed that as the tablet dissolves, the cyclodextrin particles touch the membrane and the drug is released and is passed across the membrane of the mouth into the bloodstream. Alternatively, the cyclodextrin/Ras antagonist complex can be reconsituted into an appropriate solution suitable for parenteral (e.g., intravenous or subcutaneous) administration. In general, amounts of the Ras antagonist effective for the present purposes range from about 5 mg/kg every other day to about 5 mg/kg per day. The response may be magnified by increasing the dose up to about 20 mg/kg per day in a single treatment as well as by increasing the frequency of treatment.

Timing of the administration of the Ras antagonist is important to the extent that it is in circulation so as to contact the cells before or during proliferation. In the case of restenosis, for example, the antagonist is preferably administered prophylactically such as by way of i.v. infusion at about the time of angioplasty. Administration is continued for about 14 days. In addition to i.v. administration, the agent may be formulated into a transdermal preparation such as a cream, gel or patch, or in the form of a prodrug, optionally complexed with cyclodextrin. In other embodiments, the agent is administered to a patient afflicted with the disease.

The present invention will now be described by way of the following examples. These examples demonstrate the efficacy of a Ras antagonist of the present invention to inhibit or reduce the proliferation of normal cells associated with various disease states including animal models of several autoimmune diseases, cirrhosis and restenosis. They are presented solely for purposes of illustration, and are not intended to limit the invention in any way. For ease of reading, citations of the referenced scientific publications are listed at the end of each example.

EXAMPLE 1

The Ras-Pathway Inhibitor, S-trans-trans Farnesylthiosalicilic Acid (FTS) Suppresses Experimental Allergic Encephalomyelitis This example demonstrates the inhibitory effects of FTS on acute and chronic experimental autoimmune encephalomyelitis (EAE and CR-EAE).

Experimental autoimmune encephalomyelitis (EAE) is a T-cell mediated disease that serves as a model of the acute phase of multiple sclerosis (MS) (1–3). Chronic-relapsing EAE is a model of EAE with closer clinical and histopathological resemblance to MS (4–5). Clinically, in both models of EAE, the disease is presented with acute or relapsing paralytic signs and histopathologically by lymphocytic infiltrations into the white mater of the central nervous system (CNS) and a resulting myelin destruction. T-cells are activated, following presentation of the myelin antigens by macrophages and acquire the potential to invade through the blood-brain barrier into the CNS and attack the myelin. Therefore, treatments for EAE and MS are based on immunosuppression aiming at downregulation of the proliferating myelin-reactive T-lymphocytes (6–10).

The results show that FTS suppressed EAE by downregulation of the myelin-reactive, activated T-lymphocytes. In addition, FTS did not induce generalized immunosuppressive effects. Thus, it offers significant advantages over the broad immunosuppressive modalities.

Materials and Methods

Mice

Eight week old female SJL/J mice (purchased from the Jackson Laboratory, USA) were housed under standard conditions in top filtered cages. Mice were fed a regular diet and given acidified water without antibiotics.

Antigens

Spinal cord homogenate (MSCH) from 3- to 10-month old mice of various strains were obtained by insuflation. MSCH was prepared by homogenization of the spinal cord in PBS (1:1 v/v). The homogenate was lyophilized, reconstituted in PBS to a concentration of 100 mg/ml and stored at −20° C. until used. Tuberculin purified protein derivative (PPD) was obtained from Statens Seruminstitut, Copenhagen, Denmark. Guinea pig myelin basic protein (GMBP) was prepared from guinea pig spinal cords as previously described (11). Proteolipid protein (PLP) peptide 139–151 was synthesized (12) using an automatic solid phase peptide synthesizer, in the Interdepartmental Equipment Unit, Hebrew University, Medical School (Jerusalem, Israel).

Induction and Evaluation of EAE

Induction of acute EAE was based on a modification of Bernard's protocol (13). Briefly, equal volumes of MSCH (10 mg/ml in PBS) and complete Freud's adjuvant (CFA) enriched with *Mycobacterium tuberculosis* H37Ra (6 mg/ml) (Difco Laboratories, Detroit, Mich.) were homogenized in a blender. For each mouse, 0.1 ml (0.5 mg) of the emulsion were injected s.c. into the four footpads. Immediately thereafter and 2 days later, mice were injected i.v. with *Bordetella pertussis* ($2.7 \times 10^9$ organisms per mouse) (Rafa Laboratories, Jerusalem, Israel). Animals were examined daily for signs of disease. The first clinical signs appeared on day 10–12 post immunization and were scored according to the following six point scale: 0: no abnormality; 1: mild tail weakness (floppy tail); 2: tail paralysis; 3: tail paralysis and hind leg paresis; 4: hind leg paralysis or mild forelimb weakness; 5: quadriplegia or moribund state; 6: death.

CR-EAE was induced with transfer of PLP-sensitized lymphocytes, as previously described (5). Briefly, naive SJL/J mice (8–12 weeks old) were immunized with the 139–151 peptide of PLP (150 pg/mouse) in CFA containing 400 μg of *Mycobacterium Tuberculosis*, s.c. into the flanks. On day 10 post immunization, the draining lymph nodes were removed and a single cell suspension was prepared. Lymphocytes were incubated in vitro with 400 μg/ml of the PLP peptide in full RPMI culure medium (5) for 4 days.

Thereafter the lymphocytes were injected i.v. in naive SJL/J recipients (8–12 weeks old). Each recipient animal received $60 \times 10^6$ cells. The first paralytic signs appeared on days 7–8 and the disease followed a chronic and relapsing-remitting course. All animals were examined daily and the disease severity was graded according to the above described 0–6 scale.

FTS Treatment

FTS (as powder) was diluted in chloroform (35.8 mg/ml of FTS=0.1 M) and kept in aliquods. The content (25 $\mu$l) of one aliquod was evaporated under nitrogen and then disolved in 6 $\mu$l absolute ethanol and 7 $\mu$l of 1N NaOH; 890 $\mu$l of PBS were subsequently added. Each mouse received 0.1 ml of this solution daily (0.1 mg/mouse or 5 mg/kg) intraperitoneally (i.p.).

Proliferative Response of Lymphocytes

Pooled (2–3 animals per group) single cell suspensions of lymph node cells were obtained on day 10 post EAE-induction and assayed in vitro for their response to antigens and mitogens (*Mycobacterium Tuberculosis* purified protein derivative (PPD), guinea pig myelin basic protein (GMBP), PLP 139–151 peptide, lipopolysacharide (LPS) and concanavalin (ConA) by a standard proliferative assay. The assay was carried out by seeding in each microculture well $4 \times 10^5$ cells in 0.2 ml of proliferation medium containing optimal concentrations of the following antigens: 50 $\mu$g/ml of GMBP, 50 $\mu$g/ml of PPD, 20 $\mu$g/ml of PLP peptide and 1 $\mu$g/ml of ConA. The cultures, performed in triplicate in 96-well, flat-bottom, microtiter plates (Costar, Cambridge, USA), were incubated for 72 h in a humidified atmosphere of 95% air and 5% $CO_2$ at 37° C., and then pulsed for 18 h with 1.0 microCi of $^3$H-thymidine (New England Nuclear). Cells from each microculture were harvested on fiberglass filters with a multiharvester (Dynatech Laboratories, Alexandria, Va., USA) and radioactivity was measured using standard scintillation techniques. The stimulation index (S.I.) was calculated by dividing the mean cpm of cells cultured in the presence of antigen by the mean cpm of cells cultured in the absence of antigen.

Determination of Ras in Lymphocytes

Naive SJL mice received either the vehicle or FTS (10 mg/Kg, i.p., twice a day) for 2 days. The total amounts of Ras were then determined in cell lysates prepared as detailed in (14). Briefly, spleen lymphocytes of the control and of the FTS-treated mice were homogenized in homogenization buffer as detailed previously (14–15). Total cellular protein (50 $\mu$g) corresponding to $1.2 \times 10^6$ cells, as separated by 12.5% sodium dodecylsulfate polyacrylamide gel electrophoresis (SDS-PAGE) and blotted onto nitrocellulose membranes. hmmunoblotting with pan-Ras Ab (pan-Ras Ab-3, Calbiochem), enhanced chemiluminescense assays (ECL) and densitometric analysis were then performed as detailed previously (14–15).

FACS Analysis

Single cell suspensions were prepared from the draining lymph nodes of mice in which EAE was induced, on day 10 post immunization for EAE-induction. Cells were incubated on ice, for 30 min with 20 $\mu$l of the monoclonal FITC-conjugated anti-CD62L, anti-IA-k (MHC class I) and anti-Vb17 antibodies (Becton and Dickinson, USA). The proportions of cells expressing these surface markers were examined by a fluoresecence activated cell sorter (FACS), and were calculated as the percentages of positively stained cells among 10,000 cells enumerated.

Results

FTS Inhibits Proliferation of Lymphocytes In Vitro

The first set of experiments was designed to test whether FTS inhibits the mitogenic response of lymphocytes in vitro. Lymphocytes were obtained from naive SJL mice and subjected to 3H-thymidine proliferation assays. The cells were stimulated with the potent mitogen LPS or ConA for 48 h in the absence and in the presence of various concentrations of FTS. Results of these experiments demonstrated a dose-dependent inhibition of the ConA- and LPS-induced lymphocyte proliferation, where 12.5 $\mu$M, 25 $\mu$M FTS and 50 $\mu$M FTS caused 22–50%, 66–71% and 95–98% inhibition respectively.

A second set of experiments tested whether FTS suppresses the in vitro mitogenic response in lymphocytes of EAE mice. Lymphocytes were obtained from the lymph nodes of animals immunized with MSCH for induction of EAE, on day 10 post immunization. The cells were then incubated in the absence and in the presence of various concentrations of FTS, stimulated with either LPS or with the specific myelin associated antigen, PLP 139–151 peptide. Results of a typical experiment showed that the responses to both LPS and PLP were inhibited in a dose-dependent manner by FTS. Twenty-five microM FTS were sufficient to suppress 91% and 62% of the LPS and the PLP mitogenic responses respectively.

FTS-treatment In Vivo Reduces the Amount of Ras in Lymphocytes

Lymphocytes of vehicle- and of FTS-treated (5 mg/kg/day) SJL mice were obtained from the spleens of mice, 48 h following treatment. The cells where then homogenized and the total amount of Ras was determined by Western immunobloting with pan Ras antibody (14). The apparent amount of Ras in the lymphocytes of the FTS-treated mice was lower than that of the control lymphocytes. Densitometric analysis of the data indicated that the FTS treatment caused a 36±7% reduction in the amount of Ras.

Specific Suppression of the Lymhpocytic Proliferative Responses to Myelin Antigens by FTS Treatment in EAE Mice EAE was induced in SJL mice with MSCH. The animals were divided in two groups. One group was treated i.p. with the vehicle and the other group received FTS (5 mg/Kg, i.p., daily) starting from the day of EAE-induction. Lymphocytes were obtained from the draining lymph nodes on day 10 post immunization with MSCH (before the clinical onset of the disease), and subjected to in vitro 3H -thymidine uptake proliferation assays. The cells, obtained either from the control or from the FTS-treated animals, were stimulated with mitogens in vitro for 48 h. The results of these experiments, set forth in Table 1, demonstrated a strong decrease in the reactivity of lymphocytes to the myelin antigens, PLP-peptide (72%) and GMBP (83%) in the FTS-treated mice, as compared to the controls.

TABLE 1

| | Proliferative responses of lymphocytes | | | |
|---|---|---|---|---|
| Antigens | Vehicle-treated controls (cpm) | (S.I.) | FTS-treated (cpm) | (S.I.) |
| none | 2,518 ± 564 | | 4,266 ± 508 | |
| PPD | 36,560 ± 1,650 | 14.5 | 27,342 ± 3,627* | 6.4 |
| PLP | 19,454 ± 721 | 7.7 | 8,901 ± 2,014* | 2.1 |
| GMBP | 27,724 ± 241 | 11.1 | 7,864 ± 636* | 1.8 |
| LPS | 50,410 ± 6,124 | 20.1 | 45,196 ± 4,246 | 10.6 |
| ConA | 74,973 ± 5,830 | 29.8 | 86,870 ± 7,483 | 20.4 |

*p < 0.01 (two tail t-test)
Results from one out of three repeated experiments are shown Relatively milder decreases of the reactivity to PPD (which is part of the immunizing inoculum) and to LPS (50–57%) were also observed while no change of reactivity to ConA could be detected. Taken together, these results suggest that FTS suppressed the sensitization of lymphocytes against the myelin related antigens but did not cause generalized immunosuppresive effects.

Suppression of the Expression of Membrane Cell Surface Markers of Immune Activation by FTS As shown in Table 2, fluorescence activated cell sorter (FACS) analysis of surface markers on lymphocytes from animals treated with FTS showed a reduction in the proportion of lymphocytes expressing the CD62L, the IA-k (MHC Class I) markers and the Vb17 T-cell receptor (TCR).

TABLE 2

| Cell markers/Exper. groups | CD3 | CD4 | CD8 | IA-k | Vb17 | CD62L |
|---|---|---|---|---|---|---|
| naive | 95.4 ± 3.5 | 53.3 ± 2.2 | 36.5 ± 6.3 | 16.6 ± 4.0 | 12.7 ± 5.6 | 73.1 ± 4.1 |
| EAE | 96.1 ± 3.8 | 48.2 ± 2.1 | 24.8 ± 8.2 | 32.3 ± 2.3 | 15.4 ± 2.7 | 71.9 ± 7.1 |
| EAE ± FTS | 94.2 ± 2.7 | 51.6 ± 1.9 | 26.2 ± 9.2 | 28.3 ± 3.2* | 11.3 ± 2.1* | 67.1 ± 7.3* |

*P < 0.05, two-tail t-test

The latter is thought to be one of the major TCRs expressed in lymphocytes that are responsible for the inflitrating CNS lesions in this model of EAE (16–17). These data, as well those from the proliferation assays (presented in Table 1), show that treatment with FTS down-regulates the generation of myelin (PLP)reacting lymphocytes and their activation (reduced CD62L expression).

Suppression of the Clinical Signs of EAE in FTS-treated Mice

In six separate experiments, 32 of the 38 (71.7%) vehicle-treated animals developed clinical signs of EAE compared to 16/38 (44.7%) of the FTS-treated mice (p=0.02, t-test). See Table 3. The maximal average score in the control group was 2.94±2.2, whereas in the FTS group it was significantly lower (1.63±2.2, p=0.01). Mortality was 26.3% and 10.5% in the two groups, respectively (p=0.03).

TABLE 3

Incidence and severity of EAE

| Mice groups | Incidence of EAE | Mean maximal Score | Mortality |
|---|---|---|---|
| Vehicle-treated controls | 27/38 (71.1%) | 2.94 ± 2,2 | 10/38 (26.3%) |
| FTS-treated | 17/38 (44.7%)* | 1.63 ± 2.2* | 4/38 (10.5%)* |

*: p < 0.05, two tail t-test

The clinical course of EAE in FTS-treated mice and in the control group is presented in FIG. 1. It shows that the course of EAE in FTS-treated mice was significantly ameliorated as compared to that in the controls.

Suppression of the Clinical Signs of CR-EAE in FTS-treated Mice

Figure 2:
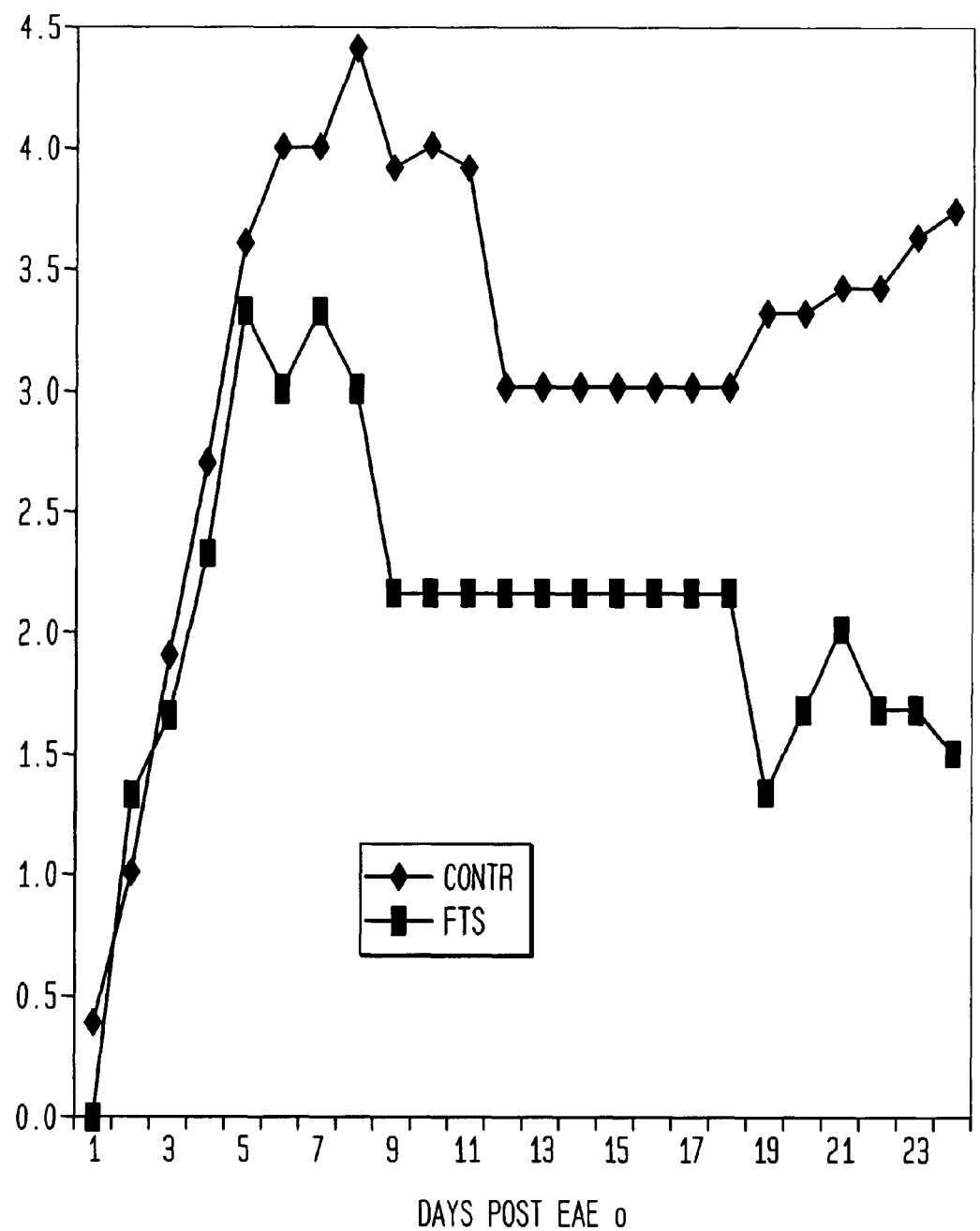
FIG. 2 is a graph that illustrates that the clinical course of chronic-relapsing EAE by FTS treatment in terms of mean clinical scores per group daily, wherein the severity of EAE was graded according to a 0–6 scale wherein the mean clinical scores per group daily.

CR-EAE was induced by passive transfer of 139–151 PLP peptide-activated lymphocytes. The recipient mice (of the PLP-activated lymphocytes) were treated with FTS (5 mg/kg/day) starting from the day of cell transfer. As shown in FIG. 2, treated mice displayed a milder form of CR-EAE (p=0.02, two-tail t-test, as compared to vehicle-treated controls) and none of them died, as compared with a mortality rate of 30% (3/10) in the vehicle-treated group. In a second experiment, mice injected with PLP-sensitized lymphocytes were followed for a period of 2–3 months for relapses of the paralytic disease (defined as an increase in the disease score for >3 days). A total of 9 relapses were observed in the control group (n=7) as compared to 5 (n=7) in the FTS-treated mice. This trend did not reach statistical significance.

Conclusions

The experimental results show that in the mouse model of acute and chronic-relapsing EAE, FTS inhibited the Ras pathway which resulted in reduced activation of lymphocytes, down-regulated the proliferation of lymphocytes against myelin antigens and suppressed the clinical paralytic signs of the disease. FTS caused a significant reduction in the amount of Ras in lymphocytes and inhibited the mitogenic response in these cells.

The finding that FTS inhibited the generation of a specific population of reactive lymphocytes is important. The data indicate that FTS inhibited the generation of myelin-reactive lymphocytes as evident by ex vivo experiments. The in-vivo clinical effects of FTS are explained and clearly manifested in vitro. Namely, a strong reduction in response to myelin specific antigens (>78% reduction) and only a mild reduction in response to non-specific antigens were observed. Thus, FTS did not cause generalized immunosuppression but rather specifically downregulated the myelin reactive lymphocytes. FACS analysis of surface lymphocytes markers in cells of animals treated with FTS provided additional evidence that the drug indeed inhibited the generation of myelin-reacting lymphocytes (those expressing the Vb17 TCR, a major and specific TCR in EAE lymphocytes (16–17). FTS also inhibited the proportions of CD62L positive cells (a marker for activated lymphocytes) and the induced—increase in IA-k. The expression of other lymphocyte cell surface markers (CD3, CD4 and CD8) was not affected by FTS in the EAE mice.

Further, FTS is more effective in cells in which Ras-GTP levels are high than in cells in which Ras-GTP levels are low. This explains the observed selectivity of FTS: lymphocytes sensitized by the myelin antigens during the induction of EAE (and thus presenting enhanced Ras activity) are more vulnerable to FTS than the rest of the lymphocytes that are not activated at that time. Thus, it is the Ras-activation that confers the selectivity of FTS in EAE. The lack of generalized immunosupressive response to FTS may therefore be attributed to insensitivity of unstimulated lymphocytes.

These in vitro effects explain the clinical efficacy of FTS treatment on EAE, both in the model of acute disease and in chronic-relapsing EAE. The later finding (that FTS can inhibit not only acute but also chronic-relapsing EAE), is of major clinical importance since CR-EAE simulates more reliably the clinical course of multiple sclerosis. The selective, non-generalized immunosuppression obtained by FTS thus provides a new therapeutic approach in MS and in other autoimmune diseases.

REFERENCES

1. Martin, R., and H. F. McFarland. 1995. lmmunological aspects of experimental allergic encephalomyelitis and multiple sclerosis. *Crit Rev Clin Lab Sci* 32:121.

2. Raine, C. S. 1994. The Dale E. McFarlin Memorial Lecture: the immunology of the multiple sclerosis lesion. *Ann Neurol* 36 (suppl.):S61.
3. Hafler, D. A., and H. L. Weiner. 1989. MS: a CNS and systemic autoimmune disease. *Immunol Today* 10:104.
4. Lublin, F. D. 1985. Relapsing experimental allergic encephalomyelitis. An autoimmune model of multiple sclerosis. *Springer Semin Immunopathol* 8:197.
5. van der Veen, R. C., J. L. Trotter, H. B. Clark, and J. A. Kapp. 1989. The adoptive transfer of chronic relapsing experimental allergic encephalomyelitis with lymph node cells sensitized to myelin proteolipid protein. *J Neuroimmunol* 21:183.
6. Karussis, D. M., and O. Abramsky. 1998. Immunomodulating therapeutic approaches for multiple sclerosis. *J Neurol Sci* 153:239.
7. Dalakas, M. C. 1995. Basic aspects of neuroimmunology as they relate to immunotherapeutic targets: present and future prospects. *Ann Neurol* 37 Suppl 1:S2.
8. Lisak, R. P. 1988. Overview of the rationale for immunomodulating therapies in multiple sclerosis. *Neurology.*
9. Karussis, D. M., S. Slavin, D. Lehmann, R. Mizrachi-Kol, O. Abramsky, and A. Ben-Nun. 1992. Prevention of experimental autoimmune encephalomyelitis and induction of tolerance with acute immunosupression followed by syngeneic bone marrow transplantation. *J. Immunol.* 148:1693.
10. Karussis, D. M., S. Slavin, A. Ben-Nun, H. Ovadia, U. Vourka-Karussis, D. Lehmann, R. Mizrachi-Koll, and O. Abramsky. 1992. Chronic-relapsing experimental autoimmune encephalomyelitis (CR-EAE): treatment and induction of tolerance with high dose cyclophosphamide followed by syngeneic bone marrow transplantation. *J. Neuroimmunol.* 39:201.
11. Diebler, G. E., R. E. Martenson, and M. W. Kies. 1972. Large scale preparation of MBP from central nervous tissue of several mammalian species. *Prep. Biochem.* 2:139.
12. Barany, G., and R. B. Merrifield. 1980. The peptide. In *The Peptide*, Vol. 2. E. Gross, and J. Meienhofer, eds. Academic Press, New York, p. 1.
13. Bernard, C. C. A., and P. R. Carnegie. 1975. Experimental autoimmune encephalomyelitis in mice: immunological response to mouse spinal cord and myelin basic protein. *J Immunol* 114:1537.
14. Haklai, R., M. G. Weisz, G. Elad, A. Paz, D. Marciano, Y. Egozi, G. Ben-Baruch, and Y. Kloog. 1998. Dislodgment and accelerated degradation of Ras. *Biochemistry* 37:1306.
15. Niv, H., O. Gutman, Y. I. Henis, and Y. Kloog. 1999. Membrane interactions of a constitutively active GFP-Ki-Ras 4B and their role in signaling. Evidence from lateral mobility studies. *J Biol Chem* 274:1606.
16. Padula, S. J., E. G. Lingenheld, P. R. Stabach, C. H. Chou, D. H. Kono, and R. B. Clark. 1991. Identification of encephalitogenic V beta-4-bearing T cells in SJL mice. Further evidence for the V region disease hypothesis? *J Immunol* 146:879.
17. Kuchroo, V. K., R. A. Sobel, J. C. Laning, C. A. Martin, E. Greenfield, M. E. Dorf, and M. B. Lees. 1992. Experimental allergic encephalomyelitis mediated by cloned T cells specific for a synthetic peptide of myelin proteolipid protein. Fine specificity and T cell receptor V beta usage. *J Immunol* 148:3776.

EXAMPLE 2

Treatment of Experimental Autoimmune Neuritis (EAN) by a Ras Inhibitor, S-farnesylthiosalicylic Acid (FTS)

This experiment shows the inhibitory effect of FTS on lymphocyte proliferation in connection with EAN.

Guillain-Barré syndrome (GBS) is the most common causes of acute generalized flaccid paralysis, with an annual incidence of 0.75 to 2 cases per 100,000 population. In Israel alone there are up to 100 new cases a year, many of them requiring respiratory support, long term intensive care hospitalization followed by rehabilitation. In spite of optimal treatment there are significant mortality and morbidity.

The pathogenesis of GBS is well characterized and involves an autoimmune post-infectious response in most cases. In contrast to the advances in the understanding of the disease, it is only in the last 10 years that effective treatments have been found for GBS. These include plasma exchange and intravenous immunoglobulins which are both expensive, do not alter the final outcome and have significant side effects.

EAN is an excellent model for the Guillain-Barre syndrome in humans. The clinical features of the animal model are very similar to the human disease, comprising a monophasic illness with ascending weakness and electrophysiological evidence for demyelinating neuropathy. This disease is especially relevant for the use of FTS since it does not respond to conventional immunosupressive treatment such as corticosteroids. The only treatments of proven efficacy in GBS are plasmapheresis and intravenous immunoglobulins.

The results indicate that FTS had an inhibitory effect on lymphocyte proliferation in vitro. In addition, various clinical and electrophysiological data demonstrate the viability of the model, and the beneficial effect of either early or late treatment.

Methods

EAN Model

The model utilized female Lewis rats which were bought at age 6 weeks and allowed to reach a weight of 200 g before entry into the study. Induction of disease was performed by immunization with peripheral myelin proteins extracted from bovine spinal roots and nerves (1). Between 5–10 mg of preparation was injected into each animal mixed with complete Freund's adjuvant with the addition of 2 mg *Mycobacterium tuberculosis* (strain H37RA; Difco). In addition to this protocol, a synthetic peptide 53–78 from the P2 protein specific for peripheral myelin (2) was also used. This provided a more homogeneous clinical response and was more specific for a demyelinating disease of the peripheral nervous system. Each treatment and control group included 5–10 rats.

Treatment Protocol

FTS was stored in chloroform which was evaporated under a stream of nitrogen. The powder was then dissolved in ethanol and diluted to the desired concentration in phosphate buffered saline made basic with NaOH. Up to 1000 $\mu$l of carrier solution containing 1–2 mg of FTS (5 mg/kg) was injected intraperitoneally into each rat. Control solution was made at the same time starting with a chloroform solution. Doses started in parallel to the initiation of disease and continued every day, 2–3 times a day, every 3 days or once a week, as well as a delayed treatment protocol starting 5 and 10 days following initiation.

Immune Tests

Cellular immune function was measured by proliferation assays utilizing labeled thymidine incorporation in response to various stimuli. These stimuli included general mitogens such as Con-A or anti-CD3 which activate T cells, LPS which activates B cells and macrophages, and specific antigens which are relevant to the model such as myelin antigens. The cells were collected from spleens and grown in 96 well plates for 72 hours in the presence of the stimulants. [$^3$H]thymidine was added and after a further 16–18 hours, the cells were harvested onto filters which were washed and counted in a scintillation counter. All assays were performed in triplicate.

Biochemical Evaluation of FTS Treatment on Ras Proteins

The amount of Ras present in the membranes and in the cytosol following FTS treatment (time course, dose dependence) was determined by Western immunoblotting with pan anti-Ras antibodies (3, 4, 5). These experiments used lymphocytes of naive rats that received the drug treatment in vitro and lymphocytes of control and of FTS-treated rats.

The advantage of the method is that it enables examination of the effects of the drugs on the membrane association of Ras proteins and on Ras-dependent signaling pathways under the same experimental conditions (i.e. growth conditions, period of drug treatment, drug concentrations). It also enables appropriate controls with isoprenoid analogues that lack growth-inhibitory activity (6). Therefore, a clear correlation between the apparent affinity of the various Ras isoforms to the membrane of lymphocytes and Ras-dependent signaling was made.

Neurological Tests

Beginning between 10–12 days post initiation, the rats generally developed progressive weakness of the tail followed by lower and then upper limbs. This progression was assessed on a standard scale of 0–9 (7). At predetermined time points the animals were sacrificed and their spinal cord and sciatic nerves were fixed for histology or frozen for biochemical assays. Motor performance was assessed by means of a Rotarod test. In this test the rats were pre-trained to run on a horizontal bar which rotates at a fixed speed. The animals were allowed to run for up to one minute in each trial and score 60" if they did so. If the animal fell from the apparatus, the latency of this event in seconds was recorded as the score for this trial. The means of 3 such trials were recorded each day the assay was performed.

Electrophysiological Tests

The animal was anesthetized with phenobarbital. Enough anaesthetic was given to ensure the procedure did not cause pain. Previous experience has shown that smaller amounts are necessary during the acute EAN disease phase in order to avoid mortality. Mono-polar needle electrodes were used to stimulate the sciatic nerve and the response was measured in the plantar muscle by a surface ring electrode (8). Alternatively, the tail nerves were stimulated and tail muscle response measured by the same electrodes. From preliminary experiments, the tail response was found to be more sensitive to the early phases of the disease while the plantar muscle response was affected at that time by injection site swelling of the lower limbs. The tail response was therefore be used in the early disease stage (days 18–22). The latency of responses to distal and proximal stimulation were used to calculate nerve conduction velocity. The amplitude of the responses was used to assess conduction block.

FTS Inhibition of Lymphocyte Proliferation In Vitro

Figure 3:
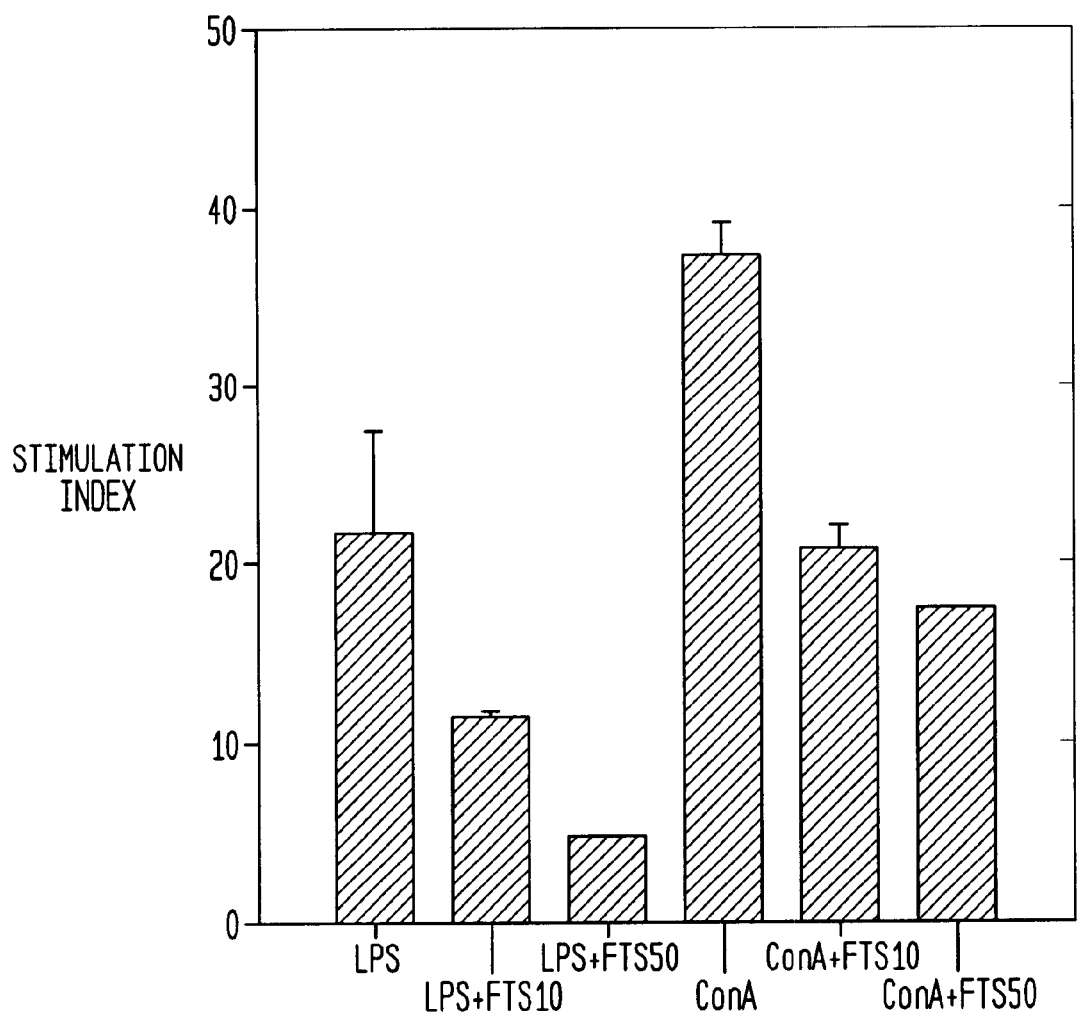
FIG. 3 is a bar graph that illustrates inhibition of splenocyte proliferation in vitro in terms of stimulation indices to LPS and ConA in the presence of 0, 10 and 50 $\mu$M FTS (+SE)

An examination was made as to whether the effect of FTS on Ras levels was of functional importance in splenocytes prepared from 2 ICR mice. Stimulation of $^3$H-thymidine incorporation into DNA was used as measure of splenocyte proliferation in the presence of lipopolysaccharide (LPS) or concanavalin A (ConA), and in the presence of 0, 10 and 50 $\mu$M FTS. The methods used are detailed below. As shown in FIG. 3, FTS produced a significant reduction of LPS and ConA induced proliferation, which was dose dependent for LPS in the concentration range of FTS used. FTS did not induce lymphocyte cell death under these conditions, evident by trypan blue exclusion staining. Also, FTS had no effect on basal $^3$H-thymidine incorporation into DNA. The concentrations of FTS at which inhibition of lymphocyte cell growth were observed reflect expected levels of the drug when given in animals at doses of 5–10 mg/kg.

Induction of EAN in Lewis Rats

The disease was induced by means of immunization with peripheral myelin obtained from bovine spinal cord roots. The normal response was from the plantar muscle to stimulation of the sciatic nerve. Distal and proximal stimulation produced a clear single wave followed by a late response, paralleling the H wave. The earliest signs of pathology were found in the tail muscle response to stimulation of the tail nerve. The amplitude of the response was lower on proximal stimulation and disappeared on distal stimulation, corresponding to a conduction block which is a common finding in humans with GBS. The H response could no longer be seen. At the peak of disease, the plantar muscle responses disappeared on distal stimulation. As the animals improved clinically, there was temporal dispersion of the muscle response followed by complete recovery 4 months following the induction.

Clinical Effect of Early FTS Treatment on EAN Rats

In a preliminary experiment, EAN was induced in 15 Lewis rats on day 0 of the experiment. Of these rats, 5 were treated with FTS, 5 mg/kg/day i.p. once daily on days 0–28. Another five rats received the same treatment on days 0–10 and 5 were sham treated with the carrier solution. FIGS. 4A and 4B summarize clinical score data and performance on a rota-rod. Treatment with FTS significantly ameliorated the peak of disease in rats continuously treated with FTS. Rats in which treatment was stopped on day 10 suffered from a disease of equal severity to controls but then recovered faster than the other groups. Three of the 5 rats in this group had brief relapses of the clinical signs during the recovery phase.

Electrophysiological Data from FTS Treated and Control Rats

Figure 5:
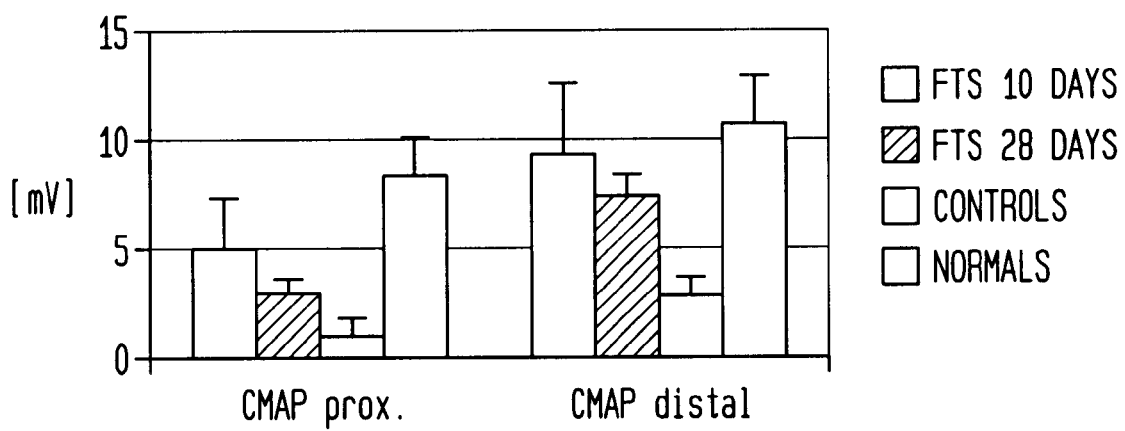
FIG. 5 is a bar graph illustrating mean (+SE) compound muscle action potentials (CMAP) evoked in the tail muscle by proximal and distal stimulation of the tail nerve in EAN rats reated with FTS for 10 and 28 days and by saline (control), and in normal (naive) rats.

Electrophysiological assays were performed on day 20 in the 3 groups of rats described in the previous section. Results obtained from stimulation of the tail nerve and measurement in the tail muscle are presented in FIG. 5. The sham treated EAN rats had significantly reduced compound muscle action potentials (CMAPs) compared to naive rats. Treatment with FTS resulted in significant amelioration of this effect, with a trend towards better results in rats treated for only 10 days.

Figure 6:
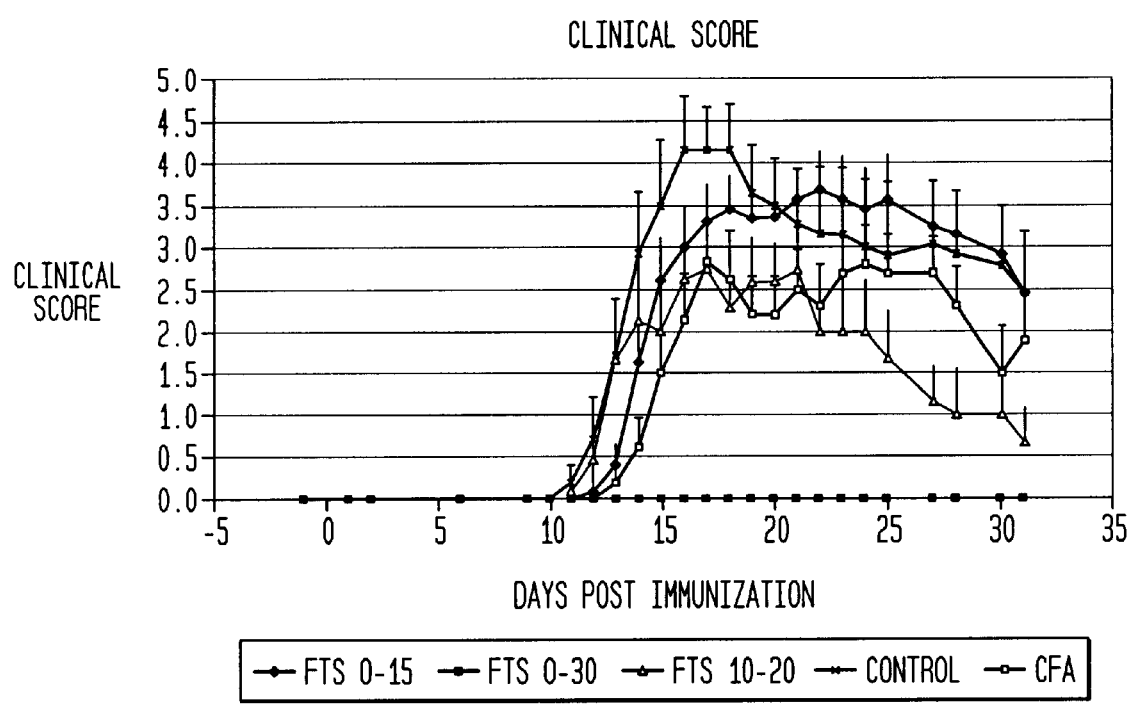
FIG. 6 is a graph illustrating mean (+SE) clinical score on the indicated days post inoculation of EAN in groups of rats (n=10) treated with FTS from day 0–15, day 0–3- or day 10–20, treated with saline (control) or immunized with adjuvant alone.

In another experiment, treatment of EAN rats from day 10 resulted in significantly less clinical signs than in untreated controls (See FIG. 6). Mean clinical scores for days 15–19 were 2.74±0.66 (±SE) in the FTS treated group compared to 4.12±0.61 (n=10 in both groups, p<0.05 by t-test). Moreover, the animals in the FTS treated EAN group recovered significantly faster than the animals in the control ENA group. This experiment also included groups (n=10) treated with FTS on days 0–28 and 0–15 days. These confirmed (p<0.001, repeated measures ANOVA at 20 days) the results presented in FIG. 4. A group immunized with the adjuvant preparation alone did not develop clinical disease though electrophysiological examination of the sciatic nerve revealed some non-specific changes (at 21 days).

REFERENCES

1. Kaladlubowski M, Hughes R A C, Gregson N A. Experimental allergic neuritis in the lewis rat: characterization of the activity of peripheral myelin and its major basic protein P2. Brain Res 1980;184:439–454.

2. Shin H C, Stuart B, McFarlane E F. Conformation of an antigenic determinant for experimental autoimmune neuritis. Biochim. Biophys. Res. Commun. 1996;224:5–9.
3. Marom M, Haklai R, Ben-Baruch G, Marciano D, Egozi Y, Kloog Y. Selective inhibition of Ras-dependent cell growth by farnesylthiosalisylic acid. J. Biol. Chem. 1995;270:22263–22270.
4. Haklai R, Weisz M G, Elad G, Paz A, Marciano D, Egozi Y, Ben-Baruch G, Kloog Y. Dislodgment and accelerated degradation of Ras. Biochemistry 1998;37:1306–1314.
5. Niv H, Gutman O, Henis Y I, Kloog Y. Membrane interactions of a constitutively active GFP-Ki-Ras 4B and their role in signaling. Evidence from lateral mobility studies. J Biol Chem 1999;274:1606–1613.
6. Aharonson Z, Gana-Weisz M, Varsano T, Haklai R, Marciano D, Kloog Y. Stringent structural requirements for anti-Ras activity of S-prenyl analogues. Biochim Biophys Acta 1998;1406:40–50.
7. Hann A F, Feasby T E, Stelle A, Lovgren D S, Berry J. Demyelination and axonal degenration in Lewis rat experimental allergic neuritis depends on the myelin dosage. Lab Invest 1988;59:115–125.
8. Cliffer K D, Tonra J R, Carson S R, Radley H E, Cavnor C, Lindsay R M, Bodine S C, Distefano P S. Consistent repeated M- and H-wave recording in the hind limb of rats. Muscle Nerve 1998;21:1405–1413.

EXAMPLE 3

Treatment of the MRL/lpr Mice, An Animal Model Of Systemic Lupus Erythematosus and Secondary Antiphospholipid Syndrome (APS), With The Ras Inhibitor Famesylthiosalicylic Acid (FTS)

This experiment was conducted to examine the effect of FTS on laboratory and clinical parameters in the MRL/lpr mouse. The MRL/lpr mouse is a genetic model of a generalized autoimmune disease similar to systemic lupus erythematosus (SLE) and the antiphospholipid syndrome (APS) in the pathology of the immune system and in systemic manifestations of the disease. The experimental results indicate that FTS lessens the manifestations of autoimmunity in this genetically determined model.

SLE and APS are relatively common chronic diseases affecting multiple organs. The etiology is not known and may involve a genetic disposition interacting with environmental factors such as infectious agents (1, 2). Effective treatments of SLE and APS include corticosteroids and antineoplastic/chemotherapeutic agents (3). The use of these agents is limited by side effects, especially in view of the chronic nature of autoimmune diseases and thus the need for prolonged administration. Experimental models of SLE and APS serve as useful tools for the investigation of the pathogenesis of the disease and the efficacy of experimental therapies. The genetically determined MRL/lpr and NZB/W mice serve as models for both systemic and neurological manifestations of SLE and APS which include circulating autoantibodies, thrombocytopenia, renal dysfunction, spontaneous abortions, motor deficits, neuromuscular disorders, cognitive deficits and behavioral changes (4, 5, 6) and high levels of Ras (7). Induced models of SLE and APS include immunization with pathogenic idiotype containing monoclonal antibodies (8, 9), or by immunization with autoantigens such as $\beta_2$-glycoprotein-1 ($\beta_2$-GPI, also known as apolipoprotein H) (10, 11, 12). Both the genetic and induced models are chronic and persistent and simulate to a large degree the course of SLE and APS. They present an opportunity to evaluate the chronic use of FTS on a wide variety of possible manifestations.

Materials and Methods

Mice

Female MRL/MpJ/lpr/lpr (MRL/lpr) mice and age-matched MRL/MpJ/+/+ (MRL/++) mice were purchased from Jackson Laboratories (Bar Harbor, Me.) at 4 weeks of age and ICR mice, aged 3 months, were obtained from Animal Resources, Sackler Medical School, Tel-Aviv University. The mice were housed in the Laboratory Animal Housing Facility at the Tel-Aviv University Medical School. This facility is maintained under standard conditions, 23±1° C., 12-hours light cycle (7 AM–7 PM) with ad libitum access to food and drink. The mice were weighed prior to the start of the experiment and weekly thereafter. The Animal Welfare Committee approved all procedures.

Drug

FTS was synthesized as previously described (13). FTS was stored in chloroform, which was evaporated under a stream of nitrogen immediately before use. The powder was dissolved in absolute ethanol and diluted to the desired concentration in sterile saline made basic with NaOH. 200 $\mu$l of carrier solution containing 100 $\mu$g of FTS (5 mg/kg) were injected intraperitoneally (i.p.) into each mouse. Control solution was prepared at the same time starting with a chloroform solution.

Mice were treated once a day, 3–5 times a week starting from 6 or 10 weeks of age until 18 weeks of age.

Spleen Lymphocyte Proliferation

Mice were killed by cervical dislocation and spleens removed with sterile precautions and placed in disposable plastic Petri dishes containing Dulbecco's phosphate-buffered saline (DPBS). Single cell suspensions were obtained by expressing DPBS through the spleen using a syringe and 19 gauge needle. The cells were suspended in DPBS and centrifuged at 1100 rpm for 7 minutes. Erythrocytes were lysed by a 7-minute incubation in 0.83% (weight/volume) ammonium chloride, and cells were immediately washed three times with DPBS. Spleen cells were suspended to a concentration of $3 \times 10^6$ cells/ml in RPMI-1640 medium containing 5% fetal calf serum (FCS), 100 units/ml penicillin, 100 $\mu$g/ml streptomycin, 2 mM L-glutamine, 0.1 mM non-essential amino acids, 1 mM sodium pyruvate, and 50 $\mu$M 2-mercaptoethanol. Cells were cultured at a concentration of $6 \times 10^5$ cells/200 $\mu$l culture medium/well in 96-well, flat-bottomed, microculture plates, and were incubated for 72 hours in a humidified atmosphere of 95% air and 5% $CO_2$ at 37° C. At the end of this time, 1 $\mu$Ci tritiated thymidine (3H-TdR) was added to each well in a 10 $\mu$l volume and the cultures were further incubated for 18 hours. Cells from each microculture were harvested on fibroglass filters with multiharvester and counted in liquid scintillation $\beta$ counter.

Mitogens and antigens were diluted to appropriate concentrations in the incubation medium and added to the wells at the beginning of incubation period to give a final concentration of 1.0 $\mu$g/ml lipopolysaccharide (LPS), 1.0 $\mu$g/ml Concanavalin A (ConA) or 10 $\mu$g/ml beta2-Glycoprotein I (beta2-GPI). Spontaneous proliferation (without mitogen or antigen) was also assessed.

To determine the effect of FTS on the splenocyte proliferation in vitro, spleen cell suspensions were prepared from 2 naive ICR mice. The splenocyte proliferation was evaluated in the presence of LPS or ConA, and in the presence of 0, 10 and 50 $\mu$M FTS.

To determine the effect of FTS on the MRL/lpr and MRL/++ mouse splenocyte proliferation ex vivo, spleen cells suspensions were prepared from three individual spleens per group, and were separately analyzed in culture (in triplicate). Splenocyte proliferation was evaluated in the presence of LPS, ConA or $\beta_2$-GPI.

The results are expressed as the mean value of stimulation index per group. The stimulation index was calculated as follows: the mean dpm of cells cultured in the presence of mitogen/antigen divided by the mean dpm of cells cultured in the absence of mitogen/antigen.

Determination of Ras in Spleen Lymphocytes

Spleen lymphocytes, obtained from six mice as described above, were pooled and plated in 10 cm dishes containing RPMI/5% FCS at a density of $2.3 \times 10^7$ cells per plate. Cultures were maintained at 37° C. in a humidified incubator (5% $CO_2$/95% air) and FTS (12.5 and 25 $\mu$M) or the vehicle (0.1% DMSO) were added one h after plating. Twenty-four hours later the cells were collected (pools of 2 plates for each treatment) and washed in PBS. The cells were then homogenized in homogenization buffer containing protease inhibitors. Ras was determined in total cell membranes (P100) and cytosol (S100) obtained by centrifugation (100,00 g, 30 min, 4° C.). Briefly, 25 $\mu$g of total cellular proteins were separated by 12.5% sodium dodecylsulfate polyacrylamide gel electrophoresis (SDS-PAGE) and blotted onto nitrocellulose membranes. Immunoblotting with pan-Ras, enhanced chemiluminescense assays (ECL) and densitometric analysis were then performed as detailed previously (14).

Serological Evaluations

The mice were bled at 16 weeks of age by retro-orbital sinus puncture and the sera were separated by centrifugation and stored at −70° C. until assayed. The sera were tested by ELISA for the presence of different autoantibodies as previously described (15, 16). This included serum dependent ($\beta_2$-GPI dependent) and independent antibodies to cardiolipin (aCL) and antibodies to single and double stranded DNA (anti-ssDNA, anti-dsDNA).

Lymphadenopathy and Splenomegaly

The development of generalized lymphadenopathy in the MRL/lpr mice (saline and FTS-treated) was evaluated by palpation of axillary and inguinal lymph nodes. The maximal lymph nodes score in each mouse was 4, when both axillary and inguinal lymph nodes (in both sides) were palpable. At 18 weeks of age the mice were sacrificed and the spleens and lymph nodes (axillary, inguinal and cervical) were removed and weighed.

Renal Function

The presence of proteinuria was measured on freshly expressed urine samples at weekly intervals. The protein content was evaluated semiquantitatively using a commercial dipstick method (Macherey-Nagel, Germany). This colorimetric assay is specific for albumin, with approximate protein concentration as follows: 0, 30, 100 and 500 mg/dl (mg%).

Rodent Neurological Examination

The four groups of mice were examined weekly using the grip strength test. Muscle strength was measured by the number of seconds the mouse was able to hang suspended on a stationary bar. A neurologically normal mouse is able to remain suspended (hang time) for 30 seconds or longer (17).

Open Field

Saline-treated and FTS-treated MRL/lpr and saline-treated MRL/++ mice (n=5), were tested for spatial behavior in a novel environment in an open field. The apparatus comprised of a circular pool (120 cm diameter by 50 cm high) placed in a lighted room. The test was conducted during the light phase of day-night cycle. The mice were brought to the experimental room 1 hour before testing. Each mouse was removed gently from its cage, placed individually at the center of the field, and videotaped with a camcorder for 20 minutes. At the end of each session the pool was cleaned with paper towels moistened with ammonium glass cleaner to remove urinary trails. The frequency and duration of progression or stopping in the open field was analyzed during playback of the video records by software custom-written by Dr. David Eilam (Life Sciences Department, Tel-Aviv University). Total distance traveled, locomotion time, speed of moving, spatial distribution of explorations and latency for establishing a home base, and duration of staying there, were extracted.

Results

Ras Inhibition in Lymphocytes In Vitro

The levels of soluble (S100) and insoluble (P100) Ras were measured by Western immunobloting with pan Ras antibodies as described in the methods. Culturing the lymphocytes in the presence of 12.5 and 25 $\mu$M of FTS resulted in a significant, dose-dependent reduction in the amount of insoluble Ras (FTS 0 $\mu$M±100±8%, FTS 12.5CM—84±9.8%, FTS 50$\mu$M—52±16%) with no concomitant observable change in the levels of soluble Ras (photographs of gels not shown).

FTS Inhibition of Lymphocyte Proliferation In Vitro

Figure 7:
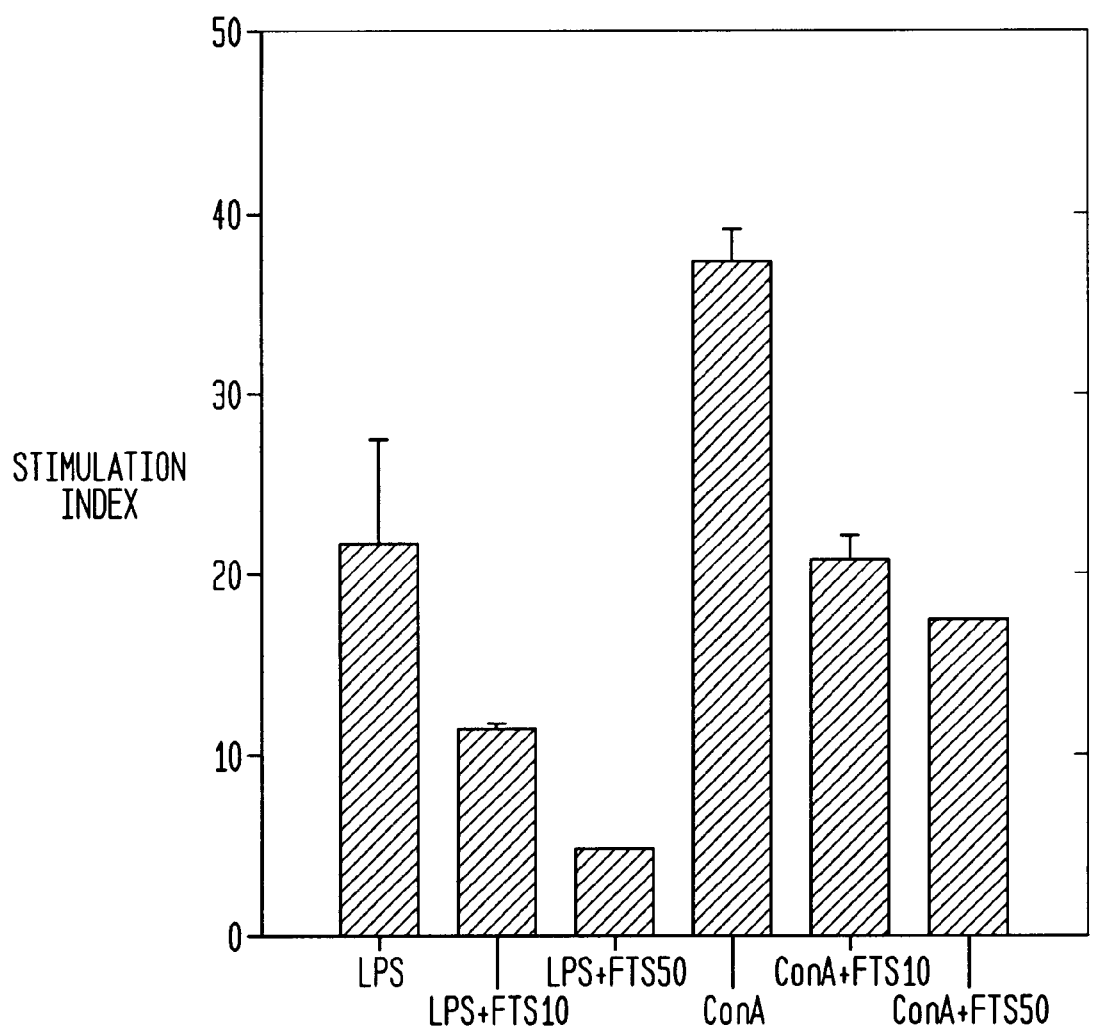
FIG. 7 is a bar graph that illustrates inhibition by FTS of normal mouse splenocyte proliferation in vitro, by measuring stimulation index to LPS and ConA in the presence of 0, 10 (FTS10) and 50 (FTS50) $\mu$M FTS determined in triplicate by uptake of 3H-TdR, and presented as the mean +SE, wherein the mean value of dpm in cells cultured in the absence of mitogen was 1192±239.

An examination was made as to whether the effect of FTS on Ras levels was of functional importance in spleen lymphocytes. Stimulation of $^3$H-TdR incorporation into DNA was used as measure of lymphocyte proliferation. Stimulation indices were measured for LPS and ConA in the presence of 10 and 50 $\mu$M FTS. As shown in FIG. 7, FTS produced a significant reduction of LPS and ConA induced proliferation, which was dose dependent for LPS in the concentration range of FTS used. FTS did not induce lymphocyte cell death under these conditions, evident by trypan blue exclusion staining. Also, FTS had no effect on basal 3H-TdR incorporation into DNA. The concentrations of FTS at which inhibition of lymphocyte cell growth were observed reflect expected levels of drug when given in animals at doses of 5–10 mg/kg. These dose levels were used in subsequent experiments in the MRL/lpr mouse/model of lupus.

Figure 8A:
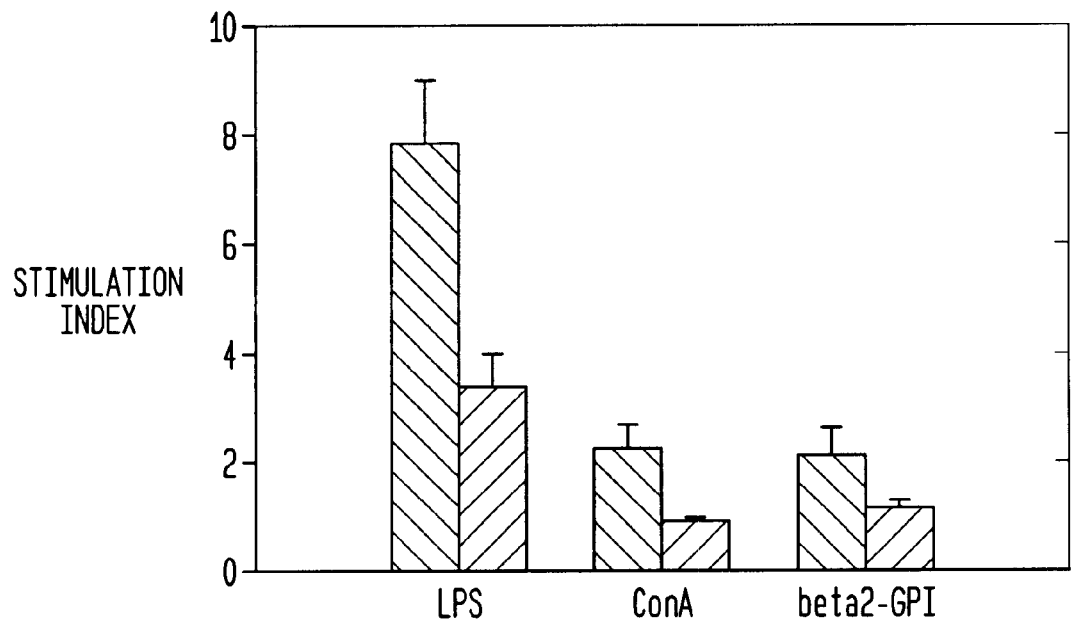
FIGS. 8A and 8B are bar graphs illustrating inhibition by FTS of MRL/lpr (8A) and MRL/++ (8B) mouse spleen lymphocyte proliferation ex vivo, by measuring mean (±SE) stimulation indices in response to LPS, ConA or beta2-GPI, wherein the mean value of dpm in cells cultured in the absence of mitogen/antigen were 3146±891 for the saline-treated MRL/lpr group (filled-hatched bars), 5321±1106 for the FTS-treated MRL/lpr group (filled bars), 5863±1382 for the saline-treated MRL/++ group (open-hatched bars) and 9092±1678 for the FTS-treated MRL/++ group (open bars)
Figure 8B:
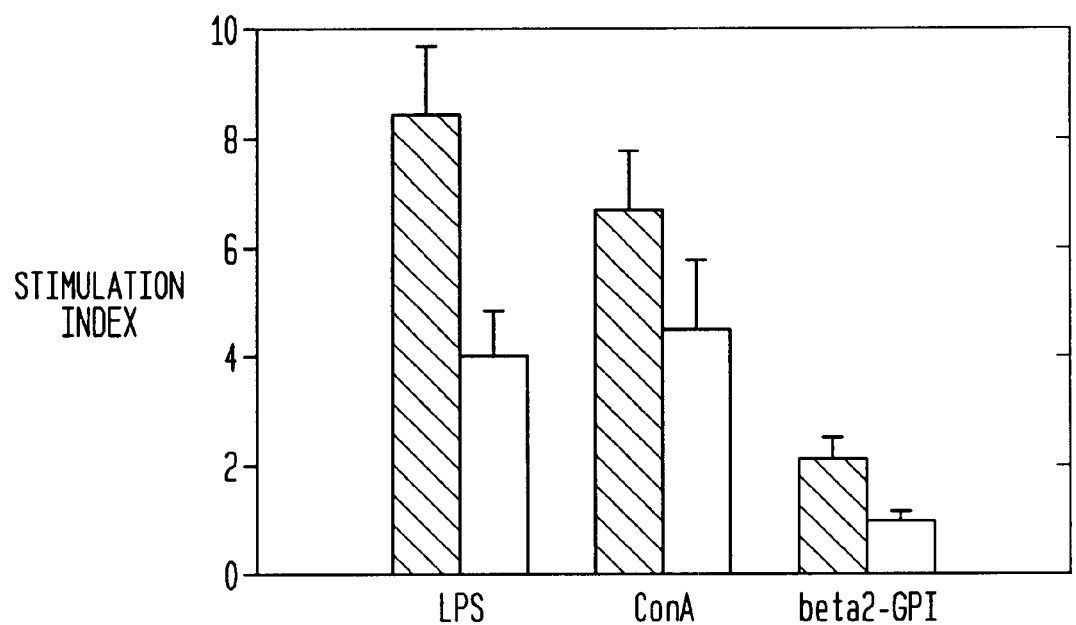

The effect of FTS on lymphocyte proliferation in vivo in MRL/lpr and control MRL/++ mice was determined by ex-vivo experiments. The mice received 5 mg/Kg FTS (5 days a week) for 3 months and spleen lymphocyte proliferation assays were then performed in vitro with no added FTS. The results are presented in FIGS. 8A and 8B. Baseline 3H-TdR incorporation was similar in all four groups examined except for a trend towards higher values in the MRL/++ mice treated with FTS. Stimulation indices reveal a two-fold reduction of the response to LPS in FTS-treated mice. As described previously (18, 19), the response of the MRL/lpr mice to ConA was markedly lower than in the MRL/++ control mice. This response was further reduced in lymphocytes of the FTS-treated MRL/lpr mice, but not in lymphocytes of the FTS-treated MRL/++. An antigen-specific proliferative response to $\beta_2$-GPI was measured and a significant 50% reduction in the response of lymphocytes of FTS-treated mice was measured in both MRL/lpr and MRL/++ mice.

Effects of FTS on Parameters of the Immune System in MRL/lpr and MRL/++ Mice

Figure 9:
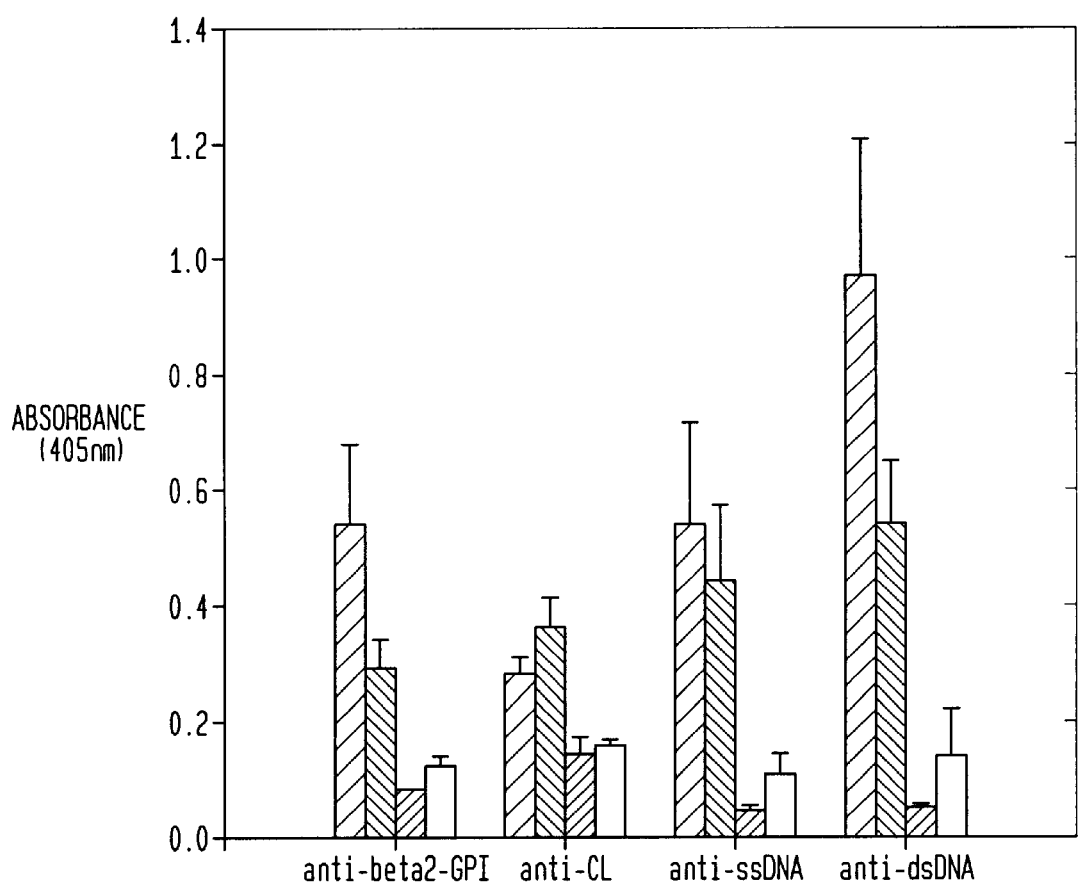
FIG. 9 is a bar graph illustrating autoantibody levels in sera of FTS-treated and saline-treated MRL/lpr and MRL/++ mice at 16 weeks of age, wherein the levels of autoantibodies are represented as mean absorbance values with standard errors, and levels of serum ($\beta_2$-GPI) dependent aCL antibodies (anti-beta2-GPI), serum-independent aCL antibodies (anti-CL), anti-ssDNA and anti-dsDNA antibodies were measured in the MRL/lpr mice (filled-hatched bars) compared to the saline-treated (open-hatched bars) and FTS-treated (open bars) MRL/++ mice.

In view of the effects of FTS on lymphocyte proliferation, mouse antibodies to relevant autoantigens including $\beta_2$-GPI dependent aCL, aCL, anti-ssDNA and anti-dsDNA, were also measured. As shown in FIG. 9, there were significantly higher levels of all these antibodies in the MRL/lpr groups compared to the MRL/++ controls ($p<0.014$ one way ANOVA). FTS treatment did lower the levels of $\beta_2$-GPI dependent aCL ($\beta_2$-GPI) antibodies and anti-dsDNA antibodies significantly in the MRL/lpr mice ($p<0.049$, one way ANOVA), however it did not affect the levels of non-serum dependent aCL and of anti-ssDNA antibodies in this group. There was a non-significant trend to higher level of antibodies in the FTS-treated compared to untreated MRL/++ mice.

Figure 10A:
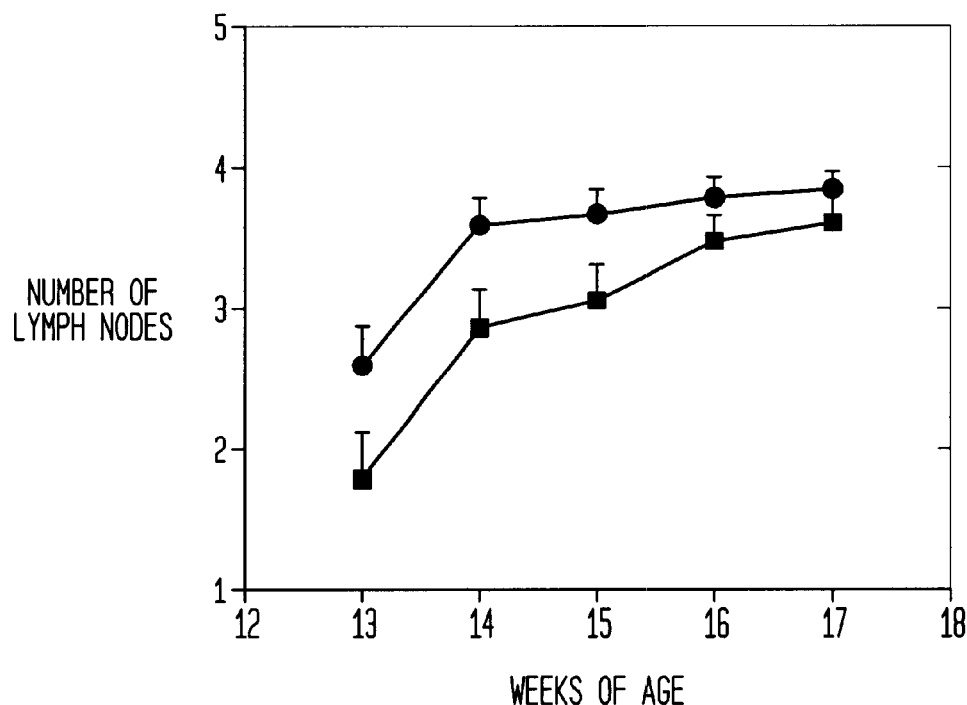
FIGS. 10A and 10B are graphs illustrating attenuation of generalized lymphadenopathy by FTS treatment in the MRL/lpr mice, wherein FIG. 10A measures adenopathy by palpation of axillary and inguinal lymph nodes and by excision, wherein values are the mean ±SE of n=16 mice in the saline-treated (circles) and n=17 mice in the FTS-treated (squares) MRL/lpr mice, and FIG. 10B measures adenopathy by weighting at 18 weeks of age.
Figure 10B:
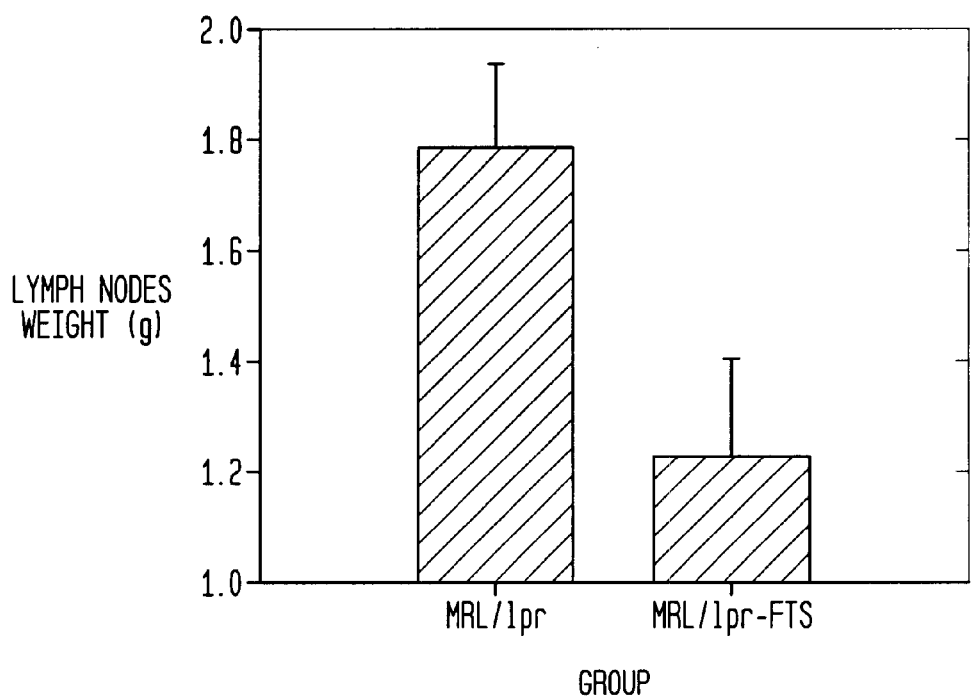

An important clinical measure of disease progression in MRL/lpr mice is lymphadenopathy. This was measured in the course of the experiments (FIG. 10A) in the MRL/lpr group and was significantly delayed in the FTS treated mice (p=0.034 by repeated measures ANOVA) though all mice developed measurable lymphadenopathy at 17 weeks of age. At this stage the animals were sacrificed and the excised lymph nodes weighed revealing a significant effect of FTS (p<0.017, one way ANOVA, FIG. 10B). Similar measurements of the spleens at 17 weeks revealed reduced weight in FTS treated MRL/lpr mice ($0.41\pm0.04$ g, mean$\pm$SE) compared to untreated mice ($0.54\pm0.04$ g, p<0.023, one way ANOVA). MRL/++ mice had smaller spleens ($0.13\pm0.01$ g) and this was not significantly affected by FTS ($0.19\pm0.03$ g).

Effects of FTS on Paramaters of Autoimmune Induced Damage in MRL/lpr Mice

Figure 11:
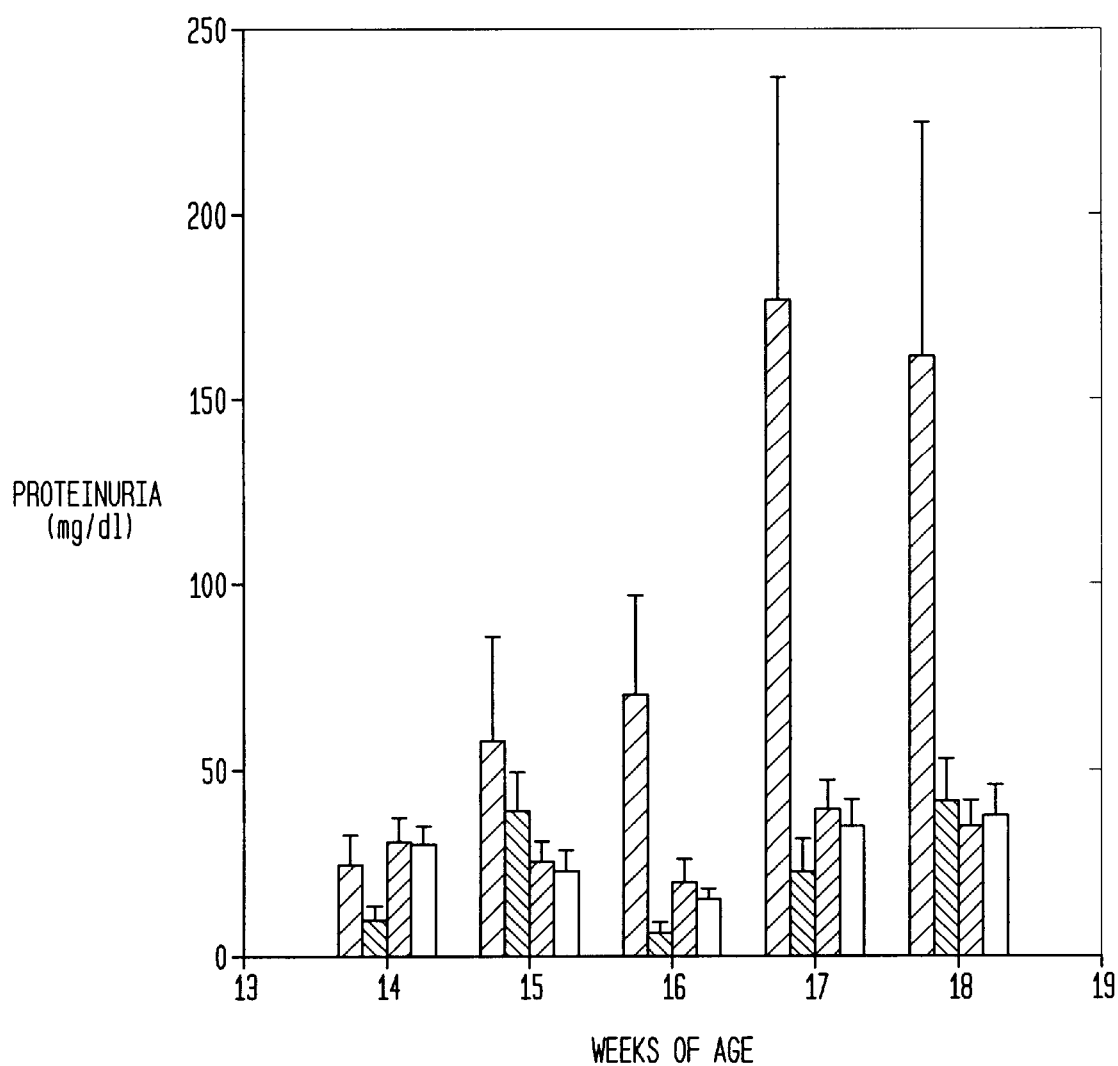
FIG. 11 is a bar graph ilustrating proteinuria (mean±SE) measured in the urine of FTS-treated and saline-treated MRL/lpr and MRL/++ mice at the indicated weeks, wherein saline-treated MRL/lpr mice (filled-hatched bars) exhibited significant proteinuria compared with trace amounts of protein detected in the FTS-treated MRL/lpr (filled bars) and MRL/++ (open-hatched bars) and saline-treated MRL/++ mice (open bars)

Proteinuria is a consistent feature of this model (20). As presented in FIG. 11, beginning at 15 weeks of age, the MRL/lpr mice developed significant proteinuria. In contrast, MRL/lpr mice treated with FTS had very low levels of proteinuria, similar to the MRL/++ group (p=0.007 by repeated measures ANOVA). The results presented are from mice (10 in each group) treated 5 days a week from 6 weeks of age. The results from mice treated from 10 weeks of age or only 3 times a week displayed a similar but less pronounced results (not shown).

Figure 12A:
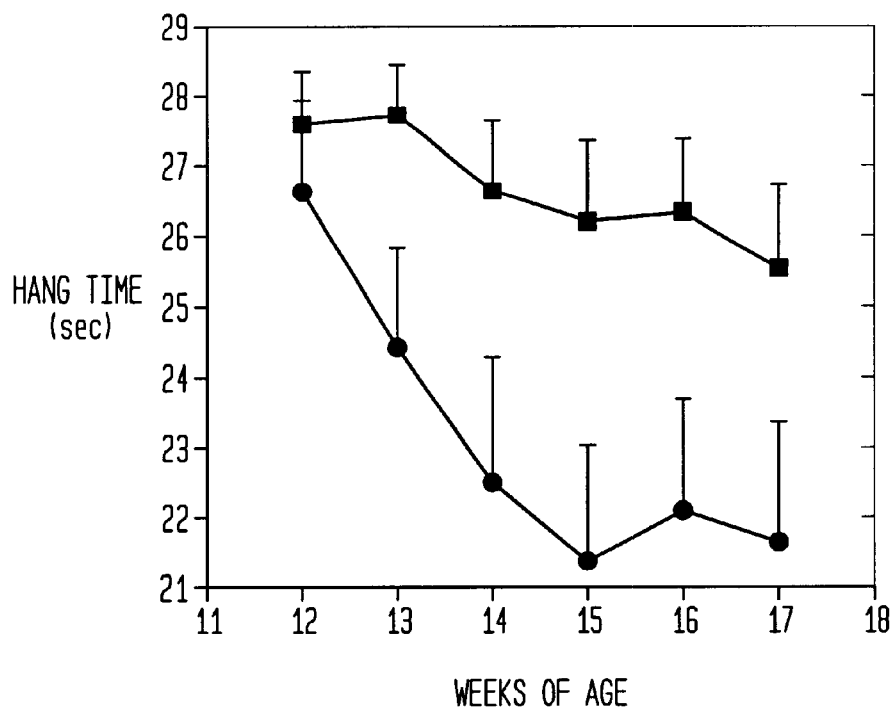
Figure 12B:
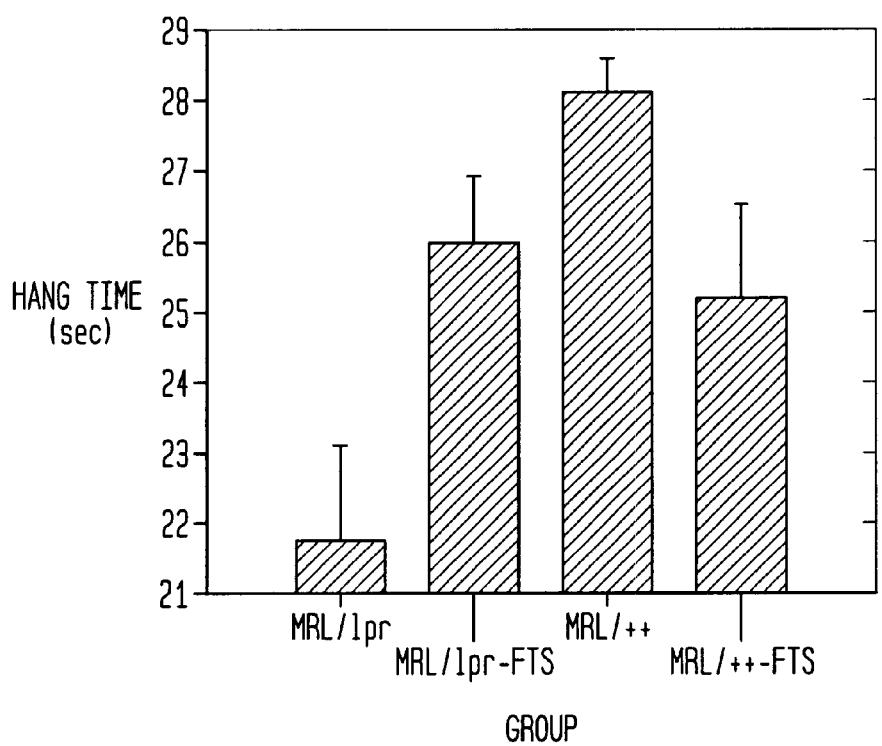

Motor function results were measured by hang time on a horizontal bar. FIG. 12A compares the time MRL/lpr mice and FTS-treated MRL/lpr mice could hang on to the bar in weekly tests from 12 to 17 weeks of age. The MRL/lpr mice were significantly impaired in this test from week 14 compared to the FTS-treated group although this group did show some decline in performance over the observation period (p<0.001 by repeated measures ANOVA). FIG. 12B summarizes the performance of all 4 groups of mice at 15–17 weeks of age. The MRL/lpr group was significantly impaired compared to the other groups (p<0.001 one way ANOVA, p<0.01 in post hoc tests) which did not differ from each other There was a trend for FTS to impair performance in the MRL/++ group.

Figure 13A:
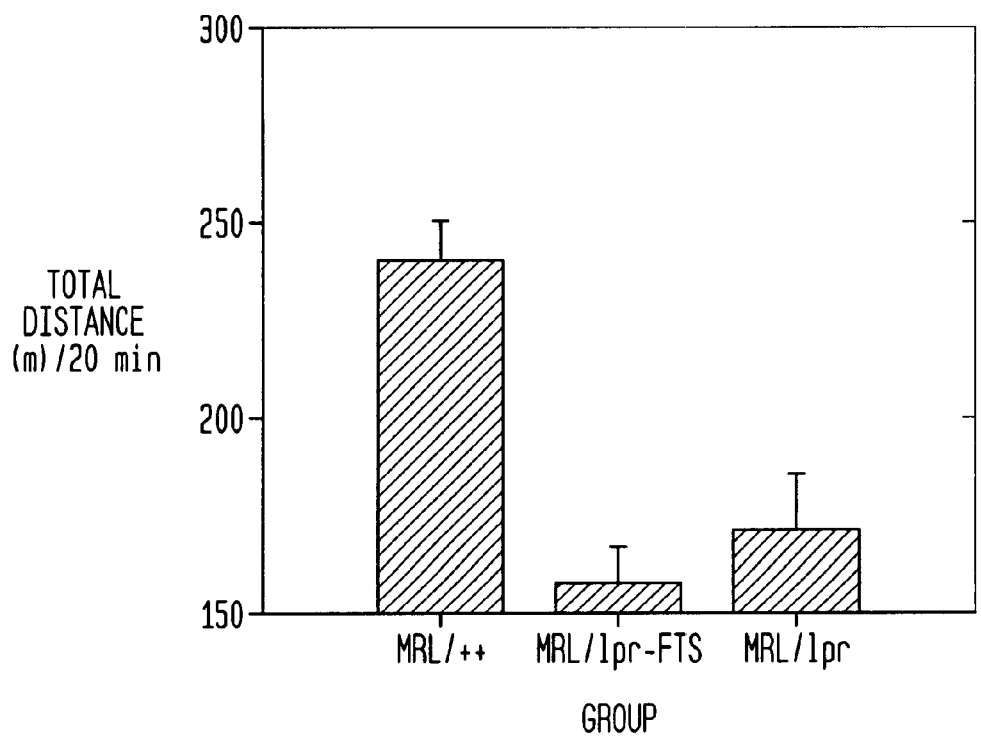
Figure 13B:
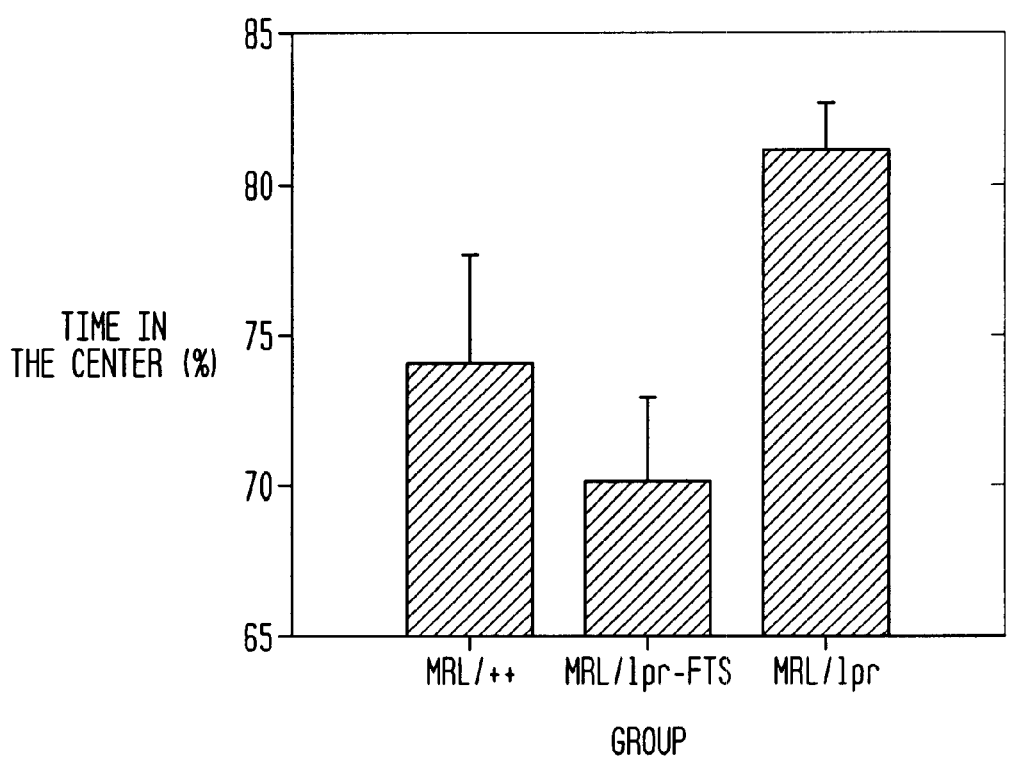

In a behavioral open field test, both FTS-treated and untreated MRL/lpr mice displayed significantly reduced locomotion compared to MRL/++ controls (p<0.001 one way ANOVA FIG. 13A). In contrast, in a purely behavioral aspect of movement, the time spent in the center of the field, there was a significant difference between the untreated MRL/lpr mice and FTS treated MRL/lpr mice (p<0.048 one way ANOVA), which were similar in their behavioral pattern to the MRL/++ controls (FIG. 13B). Thus, FTS treatment had no effect on the total distance covered, but had a significant effect on the time spent in the center of the open sield. Other measures of behavior in the open field did not reveal a beneficial, effect of FTS.

The results show that FTS treatment (5 mg/Kg/day) for periods of 6 to 18 weeks had a significant beneficial effects on the diseased MRL/lpr mouse with no significant toxicity in these mice or in the non-diseased MRL/++ control mouse. The treatment resulted in a 50% decrease in splenocyte proliferation to ConA, LPS and a disease specific antigen, $\beta_2$-GPI and in a significant decrease in serum dependent antibodies to cardiolipin and antibodies to dsDNA. Proteinuria was normalized in FTS-treated MRL/lpr mice as were grip strength and certain aspects of behavior in the open field. Lymphadenopathy and postmortem lymph node and spleen weights were significantly less in FTS treated MRL/lpr mice.

Inhibitors that directly affect Ras function have not been tested as potential selective immune system modulators in models of SLE and APS. Other studies of treatment of MRL/lpr mice include immunosuppression with corticesteroids (21) and apoptosis inducing cytoxic agents such as cyclophosphamide (21, 22) and immunomodulatory agents such as cyclosporin A (23), FK506 (22), rapamycin (23), anti-ICAM antibodies (17) and anti lymphocyte marker antibodies (24, 25). The effect of FTS on proteinuria, grip strength, antibody production, and lymphocyte stimulation compare well with results obtained with immunosuppressive and immunomodulatory drugs. In contrast, the effects of FTS on parameters such as lymphadenopathy were less pronounced.

REFERENCES

1. Shoenfeld Y, Schwartz R S. Immunologic and genetic factors in autoimmune diseases. N Engl J Med 1984;311:1019–29.
2. Shoenfeld Y, Isenberg D A. The mosaic of autoimmunity. Immunol Today 1989;10:123–6.
3. Ballow M, Nelson R. Immunopharmacology: immunomodulation and immunotherapy. JAMA 1997;278:2008–17.
4. Gharavi A E, Aron A L. Experimental models for antiphospholipid studies. Haemostasis 1994;24:204–7.
5. Shoenfeld Y. Experimental and induced animal models of systemic lupus erythematosus and Sjögren's syndrome. Curr Opin Rheumatol 1989;1:360–8.
6. Brey R L, Sakic B, Szechtman H, Denburg J A. Animal models for nervous system disease in systemic lupus erythematosus. Ann NY Acad Sci 1997;823:97–106.
7. Mendlovic S, Brocke S, Shoenfeld Y, Ben-Bassat M, Meshorer A, Bakimer R, et al. Induction of a systemic lupus erythematosus-like disease in mice by a common human anti-DNA idiotype. Proc Natl Acad Sci USA 1988;85:2260–4.
8. Shoenfeld Y. The significance of experimental models of systemic lupus erythematosus and antiphospholipid syndrome induced by idiotypic manipulation. Isr J Med Sci 1994;30:10–8.
9. Krause I, Blank M, Shoenfeld Y. Treatment of systemic lupus erythematosus and antiphospholipid syndrome: from experimental models to patients' bedside. Int Arch Allergy Immunol 1996;111:355–61.
10. Blank M, Faden D, Tincani A, Kopolovic J, Goldberg I, Gilburd B, et al. Immunization with anticardiolipin cofactor (beta-2-glycoprotein I) induces experimental antiphospholipid syndrome in naive mice. J Autoimmun 1994;7:441–55.
11. Gharavi A E, Sammaritano L R, Wen J, Elkon K B. Induction of antiphospholipid autoantibodies by immunization with beta 2 glycoprotein I (apolipoprotein H). J Clin Invest 1992;90:1105–9.
12. Garcia C O, Kanbour-Shakir A, Tang H, Molina J F, Espinoza L R, Gharavi A E. Induction of experimental antiphospholipid antibody syndrome in PL/J mice following immunization with beta 2 GPI. Am J Reprod Immunol 1997;37:118–24.
13. Marciano D, Ben-Baruch G, Marom M, Egozi Y, Haklai R, Kloog Y. Farnesyl derivatives of rigid carboxylic acids-inhibitors of ras-dependent cell growth. J Med Chem 1995;38:1267–72.

14. Haklai R, Weisz M G, Elad G, Paz A, Marciano D, Egozi Y, et al. Dislodgment and accelerated degradation of Ras. Biochemistry 1998;37:1306–14.
15. Blank M, Palestine A, Nussenblatt R, Shoenfeld Y. Down-regulation of autoantibody levels of cyclosporine and bromocriptine treatment in patients with uveitis. Clin Immunol Immunopathol 1990;54:87–97.
16. George J, Blank M, Levy Y, Meroni P, Damianovich M, Tincani A, et al. Differential effects of anti-beta2-glycoprotein I antibodies on endothelial cells and on the manifestations of experimental antiphospholipid syndrome. Circulation 1998;97:900–6.
17. Brey R L, Amato A A, Kagan-Hallet K, Rhine C B, Stallworth C L. Anti-intercellular adhesion molecule-1 (ICAM-1) antibody treatment prevents central and peripheral nervous system disease in autoimmune-prone mice. Lupus 1997;6:645–51.
18. Cameron R, Waterfield J D. Delineation of two defects responsible for T-cell hyporesponsiveness to concanavalin A in MRL congenic mice. Immunology 1986;59:187–93.
19. Dziarski R. Comparison of in vitro and in vivo mitogenic and polyclonal antibody and autoantibody responses to peptidoglycan, LPS, protein A, PWN, PHA and Con A in normal and autoimmune mice. J Clin Lab Immunol 1985;16:93–109.
20. Bernstein K A, Bolshoun D, Lefkowith J B. Serum glomerular binding activity is highly correlated with renal disease in MRL/lpr mice. Clin Exp Immunol 1993;93:418–23.
21. Kiberd B A, Young I D. Modulation of glomerular structure and function in murine lupus nephritis by methylprednisolone and cyclophosphamide. J Lab Clin Med 1994;124:496–506.
22. Woo J, Wright T M, Lemster B, Borochovitz D, Nalesnik M A, Thomson A W. Combined effects of FK506 (tacrolimus) and cyclophosphamide on atypical B220$^+$ T cells, cytokine gene expression and disease activity in MRL/MpJ-lpr/lpr mice. Clin Exp Immunol 1995;100:118–25.
23. Warner L M, Adams L M, Sehgal S N. Rapamycin prolongs survival and arrests pathophysiologic changes in murine systemic lupus erythematosus. Arthritis Rheum 1994;37:289–97.
24. Henrickson M, Giannini E H, Hirsch R. Reduction of mortality and lymphadenopathy in MRL-lpr/lpr mice treated with nonmitogenic anti-CD3 monoclonal antibody. Arthritis Rheum 1994;37:587–94.
25. Merino R, Fossati L, Iwamoto M, Takahashi S, Lemoine R, Ibnou-Zekri N, et al. Effect of long-term anti-CD4 or anti-CD8 treatment on the development of lpr CD4$^-$ CD8$^-$ double negative T cells and of the autoimmune syndrome in MRL-lpr/lpr mice. J Autoimmun 1995;8:33–45.

EXAMPLE 4

The Ras Antagonist S-trans,trans-Farnesylthiosalicylic Acid (FTS) Suppresses The Genetically Determined Antiphospholipid Syndrome (APS) in MRL/lpr Mice and in a Model of APS Induced with ApoH Glucoprotein Two models of the antiphospholipid syndrome were compared. The MRL/lpr mouse, which is a gentic model due to a mutaion in the Fas gene, and Balb-C mice immunized with ApoH ($\beta_2$ glucoprotein 1), which is an induced model. The effect of 2 months FTS (5 days per week, 5 mg/kg) treatment on autoantibody levels in MRL mice (age 10 weeks to 18 weeks) is presented in FIG. 14. The levels of autoantibodies were measured at age 18 weeks by routine ELISA assays (repeated measures ANOVA, p=0.016). Significantly lower levels of anti-ApoH and anti-double stranded DNA (dsDNA) were found in FTS treated MRL/lpr mice. Anti-ApoH and anti-dsDNA were the major autoantibody groups found. Significant, but lower levels of autoantibodies to phospholipids and single stranded DNA were found in the MRL/lpr mice compared to the MLR/++ controls. FTS did not lower significantly the level of these minor antibodies in control. FTS actually increased the levels of some autoantibodies in the control group, though to levels much lower than spontaneously seen in the MRL/lpr group.

Similar antibody assays were performed with the sera of Balb-C mice (9 per group) immunized with ApoH 10 $\mu$g in complete Freund's adjuvant with boosts given 2 and 6 weeks later in incomplete adjuvant. There was a significant effect of FTS treatment on anti-ApoH and anti-ds DNA levels and also anti-phosphatidyl-ethanolamine (not shown). Again, the levels of autoantibodies in the control group immunized with adjuvant alone were higher in the FTS treated mice, though these levels were still significantly lower than in the ApoH-immunized group.

One of the important measures of disease activity in MRL/lpr mice is proteinuria. Levels of proteinura were measured weekly by means of dip-sticks in MRL/lpr and Mrl/++ mice treated daily with FTS or with vehicle alone. Results from these assays from 12 to 18 months of age are presented in FIG. 15. Significant proteinuria developed in the MRL/lpr treated with vehicle compared to the MRL/++ groups. In contrast, the MRL/lpr mice treated with fts did not develop significant proteinuria and were indistinguishable from controls. Other systemic measures of disease activity including lymphadenopathy and lymphocyte proliferation were normalized in FTS treated MRL/lpr mice (not shown). Neurologically, weakness as measured by grip strength on a horizontal bar was impaired beginning at week 16 of age in the MRL/lpr mice and was also normalized by FTS treatment.

EXAMPLE 5

The Ras Antagonist, Farnesylthiosalicylic Acid (FTS), Inhibits Experimentally-Induced Liver Cirrhosis In Rats The aim of the present example was to examine whether FTS can prevent experimentally-induced liver cirrhosis in rats. The results indicate that inhibition of Ras expression in the liver during repeated bouts of regeneration prevents the development of experimentally induced hepatic cirrhosis.

Animals and Materials

Male Wistar rats (200–250 g), obtained from Tel-Aviv University Animal Breeding Center, were kept in the animal breeding house of the Wolfson Medical Center and fed Purina rodent chow ad libitum. All animals received humane care during the study protocol, which was in accordance with institutional guidelines. Thioacetamide (TAA) was obtained from Sigma Chemical Co. (St. Louis, Mo.).

Synthesis and Preparation of Farnesylthiosalicylic Acid (FTS)

FTS was prepared by mixing thiosalicylic acid (0.9 g, 6 mmol), guanidine carbonate (1.3 g, 7 mmol), and trans, trans-farnesyl bromide (1.7 g, 6 mmol) overnight in 75 ml of acetone at room temperature. After the acetone had evaporated, chloroform was added together with a few drops of 2 N HCl. The mixture was washed with water, and the organic phase was separated and dried on magnesium sulfate and then evaporated. The product, FTS, was purified on silica gel with mixtures of chloroform and ethyl acetate.

For each set of experiments, FTS was prepared in chloroform (0.1 M stock solution) and maintained at −70° C. The chloroform was removed from the stock solution by a stream of nitrogen prior to use, and FTS was then dissolved either in DMSO (in vitro experiments) or in ethanol (in vivo experiments). The FTS/DMSO solutions were diluted with DMEM/10% fetal calf serum (FCS) to yield a 100×drug stock solution containing 10% DMSO. A portion of this solution was applied to the cells at a dilution of 1:100. The FTS/ethanol solution was alkalinized by the addition of 1N NaOH, then diluted with phosphate-buffered saline (PBS) to obtain a solution of 1.0 mg FTS/ml (pH 8.0, 0.5% ethanol). This solution (1–1.5 ml per rat) was used in the in vivo experiments. In a separate set of experiments, the distribution of FTS in the plasma and in the liver was assayed by the use of 3H -FTS (12.5 ci/mmole, ARC, St. Louis Mo.). These experiments showed that the drug reached peak plasma levels corresponding to 10.7% of the injected dose (5 mg/Kg) and peak liver levels corresponding to 1.75% of the injected dose. The estimated concentration FTS in the liver at peak times (20 to 60 min) was 29 $\mu$M. Drug levels in the liver declined thereafter to the level of 0.5 $\mu$M at 24 h.

Induction of Liver Cirrhosis

Liver cirrhosis was induced in rats by intraperitoneal (i.p.) administration of TAA 200 mg/kg twice weekly for 12 weeks, as previously described (1, 2). Such a long term administration of TAA results in characteristic lesions that demonstrate micronodular cirrhosis in rat livers.

Induction of Acute Liver Injury

To exclude the possibility that the effect of FTS on hepatic fibrosis is due to anti-inflammatory rather than anti fibrotic activity, acute liver damage was induced by TAA (3 injections of 400 mg/kg, i.p.) in a separate group of FTS-pretreated rats. Blood was drawn 52 h after the first TAA injection for the measurement of serum levels of hepatic enzymes and blood ammonia, and liver tissue was prochistopathologic assessment.

Experimental Design

The FTS was dissolved in PBS and administered i.p. 3 times a week to rats according to their assigned groups. Four groups containing 6 rats each were treated as follows. One group received TAA 200 mg/kg i.p. twice a week and i.p. injections of PBS 3 days a week for 12 weeks (cirrhotic controls for the FTS-treated groups). A second group received TAA for 12 weeks and FTS 5 mg/kg, 3 times a week. This dose was chosen in light of previous animal studies showing that FTS at doses of 3–10 mg/Kg effectively inhibited tumor growth. The two control groups consisted of one that received PBS injections without TAA for 12 weeks (normal controls) and a group of 5 rats that received only FTS 5 mg/kg i.p. for 12 weeks to monitor the appearance of adverse effects.

Analysis of Liver Histopathology

The rats were sacrificed at the completion of the treatment protocols. Their livers were removed and midsections of the left lobes of the livers were processed for light microscopy. This processing consisted of fixing the specimens in a 5% neutral formol solution, embedding the specimens in paraffin, making sections of 5 $\mu$m thickness, and staining the sections with hematoxylin and eosin. Reticulin stain was performed to enhance the visualization of the extent and distribution of liver fibrosis. The tissue slices were scanned and scored by two expert pathologists who were not aware of the sample source. The degree of inflammation and fibrosis was expressed as the mean of 10 different fields in each slide that had been classified on a scale of 0–3 according to Muller, et al(3).

Measurement of Hepatic Hydroxyproline Levels

Quantitative determination of hepatic hydroxyproline levels was performed as previously described (2). The hydroxyproline levels were analyzed twice and separately for each liver.

Measurement of Ras Expression

Figure 17:
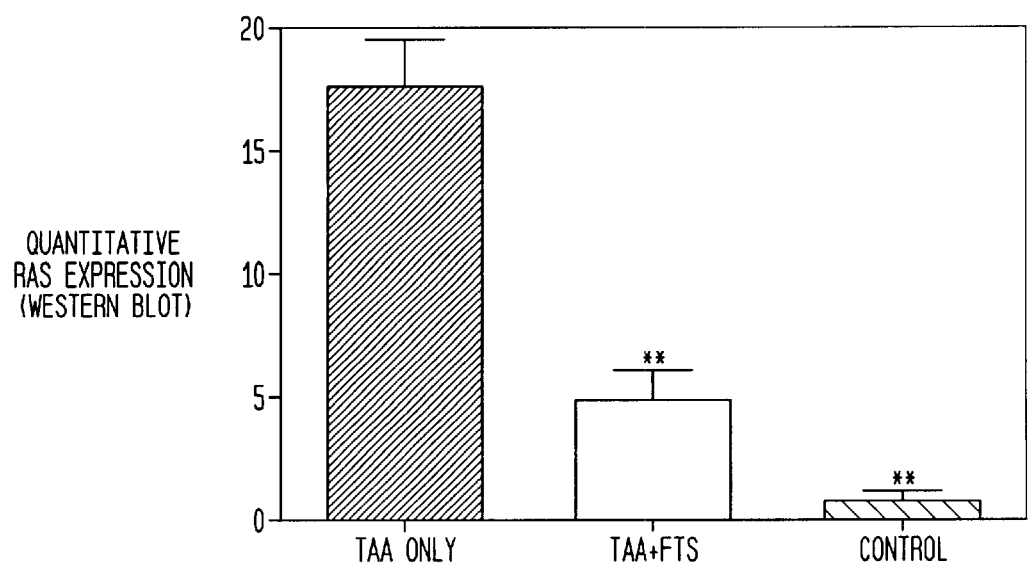
FIG. 17 is a bar graph that illustrates quantitative Ras expression determined by Western blot analysis expressed as OD percentage/control.

The levels of Ras proteins in the rat livers were determined by immunoblotting assays using anti Ras antibodies (PanRasAb03, Santa Cruz) as detailed previously (4, 5). Briefly, the livers were homogenized (10% w/v) in 0.32M sucrose, 50 mM Tris HCl, pH 7.4 buffer containing 3mM EDTA, 1 mM EGTA, 5 $\mu$g/ml pepstatine, and 5 units/ml opsotonin. Nuclei and cell debris were removed by a 10-minute 1000×g spin. The plasma membrane-enriched fraction was obtained by a 20,000×g 30 minute spin. The resulting pellets were resuspended in homogenization buffer and samples containing 20 $\mu$g proteins were used for 12.5% SDS-PAGE (mini gels). The gels were subjected to immunoblotting assays as described previously (4). Each western blot was analyzed 3 times and the data in FIG. 17 represent the means±SD OD of these 3 blots. Ras was also determined by immunohistochemistry.

Isolation and Culture of Human Stellate Cells

Human HSCs were isolated from wedge sections of normal human liver unsuitable for transplantation as previously reported (6, 7). Briefly, after a combined digestion with collagenase/pronase, HSCs were separated from other liver nonparenchymal cells by ultracentrifugation over gradients of stractan (Cellsep™ isotonic solution, Larex Inc., St. Paul, Minn.). Extensive characterization was performed as described in (7). Cells were cultured on plastic culture dishes (Falcon, Becton Dickinson, Lincoln Park, N.J.) in Iscove's modified Dulbecco's medium supplemented with 0.6 U/ml insulin, 2.0 mmol/L glutamine, 0.1 mmol/L non-essential amino acids, 1.0 mmol/L sodium pyruvate, antibiotic antifungal solution (all provided by Gibco Laboratories, Grand Island, N.Y.) and 20% fetal bovine serum (Imperial Laboratories, Andover, U.K.). Experiments described in this study were performed on cells between third and fifth serial passages (1:3 split ratio) using three independent cell lines. As previously reported (7), at these stages of culture, human HSC showed transmission electron microscopy features of "myofibroblast-like cell", thus indicating complete transition to their activated phenotype.

DNA Synthesis

DNA synthesis was measured as the amount of [Methyl-$^3$H]thymidine ([$^3$H]TdR) incorporated into trichloroacetic acid-precipitable material. Cells were plated in 24-well dishes at a density of 2×10$^4$ cells/well in complete culture medium containing 20% FBS. Confluent cells (approximately 1×10$^5$ cells/well) were incubated in serum-free/insulin-free (SFIF) medium for 24 h and then for additional 24 h in fresh SFIF containing different concentrations of FTS. Cells were then stimulated with 10 ng/ml of PDGF-BB for 20 h and then pulsed for an additional 4 h with 1.0 $\mu$Ci/ml [$^3$H]TdR (6.7 Ci/mmol). At the end of the pulsing period, [$^3$H]TdR incorporation into cellular DNA was measured as previously reported (8). Cell number was determined in three separate wells from each dish and results were expressed as cpm/10$^5$ cells.

Chemotactic Assay

Cell migration was carried out as previously described (9, 10). Briefly, the experiments were performed using a modified Boyden chamber technique equipped with 8 $\mu$m porosity polyvinylpyrrolidone-free polycarbonate filters (13 mm diameter). Polycarbonate filters were precoated with 20 µg/ml of human type I collagen for 30 min at 37° C. and placed between the upper and the bottom chamber. Confluent HSC in 6 well/dishes were incubated in serum-free/insulin-free (SFIF) medium for 24 h and then for additional 24 h in fresh SFIF containing different concentrations of FTS. They were then suspended by mild trypsinization (0.05% trypsin/EDTA). An aliquot (210 µl) of the obtained cell suspension, corresponding to $4 \times 10^4$ cells, was added to the top well and incubated at 37° C. for 6 h. The lower chamber was filled with serum-free/insulin-free medium (control) or PDGF-BB (10 ng/ml). After fixing in 96% methanol and staining with Harris' hematoxylin solution, cells that migrated to the underside of the filters were quantitated as the mean number of cells in 10 high-power fields (HPF). All experiments were run in triplicate. Each triplicate assay was repeated two times on separate occasions with different HSC preparations. Possible cytotoxic effects were monitored by the trypan blue exclusion test.

Statistical Analysis

Results, relative to the number of experiments indicated, are expressed as means±SD. Statistical analysis of in vitro experiments was performed by one-way ANOVA, and, when the F value was significant, by Duncan's test. Unless otherwise specified, P values lower than 0.05 were considered statistically significant. The significance of differences between different experimental groups in vivo was determined by Student's t-test.

Results

Inhibition of Liver Cirrhosis in Rats by FTS

Intraperitoneal administration of TAA for 12 weeks resulted in a uniform fine granulation of the surface of the rat livers. Microscopic analysis revealed cirrhotic-like structural patterns characterized by mixed-sized fibrotic nodules in these TAA-treated rats. In contrast, the livers of rats that received TAA and FTS for 12 weeks showed only slight portal and peri-portal inflammation with mild bridging fibrosis, but no cirrhotic nodules (0.8±0.5 vs 2.6±0.5, p<0.001 Table 4) or fibrotic septa (0.9±0.5 vs 2.7±0.5, p<0.001, Table 4). These findings indicate that the Ras antagonist, FTS, inhibits the development of TAA-induced liver cirrhosis in rats.

TABLE 4

The effects of FTS on liver histopathology of *TAA-treated rats

| Compound used for treatment | FTS (mg/kg) | Nodule formation (0–3)** | Fibrotic septa (0–3)** |
|---|---|---|---|
| FTS | 5 | 0 | 0 |
| TAA + NaCl 0.9% | — | 2.5 ± 0.7 | 2.7 ± 0.8 |
| TAA + FTS | 5 | 0.7 ± 0.6 | 0.9 ± 0.5 |

*TAA; 200 mg/kg i.p. twice weekly for 12 weeks.
**Scale of 0–3: no change = 0; slight changes = 1; stronger changes = 2; intense changes = 3. FTS (5 mg/kg) was administered 3 times/week for 12 weeks.

Hepatic Hydroxyproline Content

Figure 16:
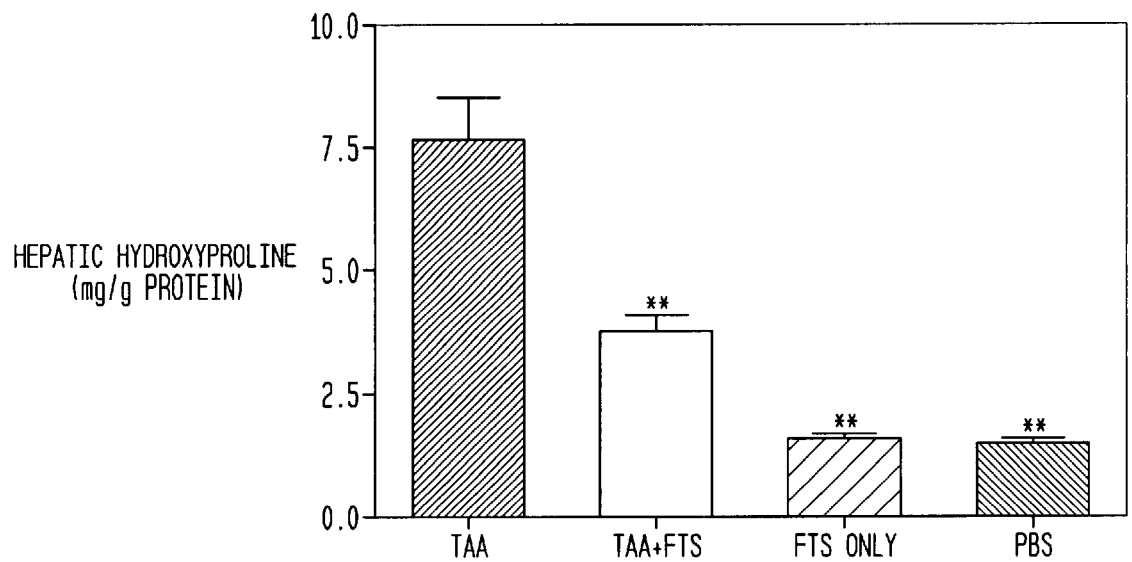
FIG. 16 is a bar graph that illustrates the effect of FTS, on hepatic hydroxyproline in thiacetamide-induced liver cirrhosis in rats, wherein hydroxyproline is expressed in mg/g protein, and Mean±SD, n=6 in each group, p<0.01, compared to TAA.

Hepatic fibrosis was quantitated by the measurement of hepatic levels of hydroxyproline. As illustrated in FIG. 16, the mean hydroxyproline levels of the TAA-treated group were significantly higher than those of the TAA plus FTS and the control groups (7.7±0.9 vs. 3.8±0.5 mg/g protein, p=0.007, compared to 1.6±0.1 mg/g protein in the control group treated with FTS only. These quantitative measurements are well correlated with the qualitative histopathologic scoring.

Quantitative Ras Expression

Ras levels in membranes extracted from the rat livers were measured by Western blot analysis using pan anti-Ras antibodies. As shown in FIG. 17, the TAA-treated group showed a 17.6±2.0-fold increase in Ras levels as compared to the control group, whereas the Ras levels were only 4.9±1.2-fold higher than those of the control group in the TAA+FTS treated group. Similar results were obtained when whole liver homogenates were tested. Accordingly, the FTS treatment caused a 70% decrease in Ras expression in the livers of the TAA-treated rats.

Rats Survival

After 12 weeks of TAA administration none of the rats died in either the group of rats treated with TAA only, or in the group of rats treated with TAA+FTS (n=6 in each group).

Lack of Inhibition of TAA-induced Acute Liver Damage by FTS

To exclude the possibility that the inhibition of hepatic fibrosis by FTS was due to decreased inflammation and cell necrosis, we used TAA and FTS in a model of acute hepatic necrosis. As shown in Table 5, FTS did not prevent liver necrosis in response to acute TAA administration, as manifested by the elevation of hepatic enzymes and blood ammonia levels. These results indicate that the inhibition of hepatic fibrosis by FTS is not due to diminished inflammation and cell necrosis.

TABLE 5

Lack Of Effect Of FTS On Hepatic Inflammation And Necrosis Induced By Acute Administration Of TAA

|  | AST (IU/l) | Blood Ammonia (µg/ml) | Hepatic inflammation and cell necrosis (score of 0–3) |
|---|---|---|---|
| TAA | 3018 ± 1014 | 7.8 ± 2.0 | 2.3 ± 0.7 |
| TAA + FTS | 2996 ± 364 | 8.9 ± 2.3 | 2.5 ± 0.6 |

Mean ± SD, n = 5 in each group. The differences between the two groups are not statistically significant in any of the above parameters.

TAA was administered in 3 consecutive injections of 400 mg/kg, i.p. in 24 h intervals. Serum levels of liver enzymes, blood ammonia and liver histology were determined 52 h after the first TAA injection. FTS administration (5 mg/kg daily), was started 3 days prior to the first TAA injection.

Lack of FTS Side Effects

In order to monitor the presence of adverse effects caused by the prolonged administration of FTS, a control group received the Ras antagonist for 12 weeks. At the end of treatment, no mortality or major adverse effects were observed in the treated rats. Blood chemistry, including liver, kidney and thyroid functions, and complete blood count were within the normal range. Liver histology in this group appeared completely normal (See Table 4). These results are in accordance with earlier studies which demonstrated no alteration in body weight, specific organs size, blood count and chemistry in FTS-treated animals. Nevertheless, these preliminary results do not entirely exclude potential side effects which may appear following longer periods of administration of Ras antagonists, and further toxicity studies would be necessary to adequately determine the safety of FTS administration.

Effects of FTS on HSC Activation

To examine the possibility that the inhibition of liver cirrhosis by FTS can be associated with the inhibition of stellate cell activation, human HSC were used in culture (6, 7, 8). In the first set of experiments, the effects of FTS on PDGF-stimulated 3H-thymidine incorporation into DNA in HSC were examined. The results of these experiments indicated that FTS (25–50 µM) the PDGF-stimulated 3H-thymidine incorporation into DNA in HSC. In the second set of experiments, an examination was made as to whether FTS can affect PDGF-induced cell migration. Results of these experiments demonstrated that the HSC were highly sensitive to FTS where 2.0–2.5 µM FTS inhibited (50%) the PDGF-stimulated cell migration.

Conclusions

Hepatic fibrosis occurs when there is an imbalance between matrix synthesis and degradation, leading to a net increase in the deposition of extracellular matrix. During this fibrotic process, extracellular matrix components, such as collagens, non-collagenous glycoproteins and proteoglycans, accumulate in the intercellular space of the liver. Early in the fibrogenic process, HSC, in response to cytokines such as PDGF and TGF-β, proliferate and deposit matrix components in the extracellular space (11, 12, 13, 14).

FTS was examined to determine whether it can affect growth-factor stimulated HSC migration and proliferation and inhibit the development of liver fibrosis induced by chronic administration of TAA. Shortly after administration, it undergoes extensive metabolism (15), by the mixed function oxidase system. It is believed that free radical-mediated lipid peroxidation contributes to the development of TAA-induced liver fibrosis. In chronic TAA intoxication, substantial liver fibrosis and prominent regenerative nodules were shown to develop after 3 months of TAA administration, associated with portal hypertension and hyper-dynamic circulation characteristic of liver cirrhosis (3).

The results show that FTS inhibited in a dose dependent manner PDGF-induced activation of HSC in vitro consistent with the above noted mode of FTS action on Ras proteins and with the possibility that FTS can also inhibit the development of liver cirrohsis. Indeed, when administered 3 times a week at a relatively low dose (5 mg/kg), FTS inhibited the development of liver cirrhosis in rats chronically treated with TAA and induced a reduction in the amount of hepatic Ras. The inhibition of liver fibrosis, as assessed by light microscopy, correlated with measurements of hepatic hydroxyproline levels. Moreover, Ras levels were also markedly decreased in the livers of rats treated with TAA and FTS as compared with those treated with TAA only. No apparent side effects attributable to FTS were observed in a group of rats that received only the Ras antagonist for 12 weeks. To elaborate on the mechanism of the inhibition of liver cirrhosis by FTS, additional experiments were performed that showed the failure of FTS to prevent liver inflammation and necrosis induced by acute administration of TAA. These results indicate that the decrease of hepatic fibrosis by FTS is not due to inhibition of inflammation and cell necrosis.

REFERENCES

1. Hori N, Okanoue T, Sawa Y, Mori T, Kashima K. Hemodynamic characterization in experimental liver cirrhosis induced by thioacetamide administration. Dig Dis Sci 1993; 38:2195–202.
2. Woessner J F. The determination of hydroxyproline in tissue and protein samples containing small proportions of this imino acid. Arch Biochem Biophys 1961;93:440–447.
3. Muller A, Machnik F, Zimmermann T, Schubert H. Thioacetamide-induced cirrhosis-like lesions in rats—usefulness and reliability of this animal model. Exp Pathol 1988;34:229–36.
4. Marom M, Haklai R, Ben-Baruch G, Marciano D, Egozi Y, Kloog, Y. Selective inhibition of ras-dependent cell growth by farnesyl thiosalicylic acid. J Biol Chem 1995;270:22263–22270.
5. Haklai R, Gana-Weisz M, Gilad G, Marciano D, Egozi Y, Ben-Baruch G, Kloog, Y. Dislodgment accelerated degradation of Ras. Biochemistry 1988; 37: 1306–13014.
6. Pinzani M, Failli P, Ruocco C, Casini A, Milani S, Baldi E, Giotti A, and Gentilini P. Fat-storing cells as liver-specific pericytes: spatial dynamics of agonist-stimulated intracellular calcium transients. *J Clin Invest* 1992; 90:642–646.
7. Casini A, Pinzani M, Milani S, Grappone C, Galli G, Jezequel A M, Schuppan D, Rotella C M, Surrenti C. Regulation of extracellular matrix synthesis by transforming growth factor-β1 in human fat-storing cells. *Gastroenterology* 1993; 105:245–253.
8. Pinzani M, Gesualdo L, Sabbah G M, Abboud H E. Effects of platelet-derived growth factor and other polypeptide mitogens on DNA synthesis and growth of cultured liver fat-storing cells. *J Clin Invest* 1989; 84:1786–1793.
9. Marra F, Gentilini A, Pinzani M, Ghosh Choudhury G, Parola M, Herbst H, Laffi G, Abboud H E, Gentilini P. Phosphatidylinositol 3-kinase is required for platelet-derived growth factor's action on hepatic stellate cells. *Gastroenterology* 1997; 112:1297–1306.
10. Carloni V, Romanelli R G, Pinzani M, Laffi G, Gentilini P. Expression and function of integrin receptors for collagen and laminin in cultured human hepatic stellate cells. *Gastroenterology* 1996; 110:1127–1136.
11. Schuppan D, Somasundaram R, Just M. The extracellular matrix: a major signal transduction network. In: B. Clement, A. Guillouzo, eds. Cellular and Molecular Aspects of Cirrhosis. Paris: John Libbey Eurotext, Les Editions INSERM 1992;216:115–34.
12. Clement B, Loreal O, Rescan P Y, Levavasseur F, Diakonova M, Rissel M, L'Helgoualc'h A, Guillouzo A. Cellular origin of the hepatic extracellular matrix. In: Gressner A M, Ramadori G, eds. Molecular and Cell Biology of Liver Fibrogenesis. Dordre: Kluwer Academic Publishers 1992; 85–98.
13. Ogawa K, Suzuki J, Mukai H, Mori M. Sequential changes of extracellular matrix and proliferation of Ito cells with enhanced expression of desmin and actin in focal hepatic injury. Am J Pathol 1986;125:611–19.
14. Dashti H, Jeppsson B, Haggerstrand I, Hultberg B, Srinivas U, Abdulla M, Bengmark S. Thioacetamide- and carbon tetrachloride induced-liver cirrhosis. Eur Surg Res 1989;21:83–91.
15. Chieli E, Malavldi G. Role of the microsomal FAD-containing monooxygenase in the liver toxicity of thioacetamide S-oxide. Toxicology 1984;31:41–52.

EXAMPLE 6

The Effect of FTS on Intimal Hyperplasia in a Model of Carotid Balloon Injury in the Rat The aim of this experiment was to investigate the effect of FTS on intimal hyperplasia in a rat carotid balloon injury, as an indication of whether FTS can ameliorate restenosis by reducing smooth muscle cell proliferation and migration. The results indicate that FTS appears to be a potent inhibitor of intimal hyperplasia.

Artherosclerosis and restenosis are two processes that involve cellular proliferation that eventually lead to functional narrowing of blood vessels causing considerable morbidity and mortality (1–4). The formation of neointimal following balloon denudation is thought to involve proliferation and migration of medial smooth muscle cells or modified adventitial fibroblasts (4, 5, 6, 7). In recent years, evidence has also accumulated pointing towards the involvement of the immune system in artherosclerosis and restenosis, as manifested by the local presence of activated T lymphocytes (3, 4) and elevation of inflammatory markers such as CRP, IL-6 and other markers (8–10).

The long-term effectiveness of percutaneous balloon coronary angioplasty (PTCA) and stent implantation is still largely limited due to the occurrence of late lumen loss following intimal thickening. Although several experimental strategies have provided some success in reducing intimal thickening in animals, clinical trials in humans performed so far failed to achieve significant improvement (10–17). Effective clinical utility in reducing the rate of restenosis was recently shown only for intracoronary radiation therapy (18–19).

Methods

Animals

Male Wistar rats 6 weeks old (weighing 250–280 gr). The animals were purchased from the Tel Aviv University and maintained at the local animal house.

Study Design

Group A: Four rats received daily intraperitoneal injections of FTS (5 mg/Kg) starting from the day of injury induction until sacrifice, 14 days later.

Group B: Four rats received daily intraperitoneal injections of control vehicle starting from the day of injury induction until sacrifice, 14 days later.

Rat Carotid Injury Method

Animals were anesthetized by intraperitoneal injection of Ketamin (80 mg/Kg) and Xylazine (5 mg/Kg). Endothelial denudation and vascular injury was achieved in the left common carotid artery, as described (6). Briefly, a balloon catheter (2F Fogarty) was passed through the external carotid into the aorta; the balloon was inflated with sufficient water to distend the common carotid artery and then pulled back to the external carotid. This procedure was repeated three times, and then the catheter was removed. After 14 days, the animals were sacrificed and the right and left carotid arteries were taken out and fixed in 4% paraformaldehyde until embedding in Paraffin. The arteries were cut in 10 um sections and stained with H&E and computer-assisted morphometric analyses were performed. The tested parameters were: intimal area, medial area, intimal/medial ratio and lumen area. Additionally, the %CSAN-N (% cross sectional area neointimal-neointamal) was calculated [IEL area-Lumen area]×100/IEL (a measure of the degree to which the IEL area is reduced by neointimal with greater normalization of the effect of changes in vessel wall size. Vasular remodeling process were further evaluated by computing the amount of plaque relative to the EEL (external elastic lamina) area.

Immunohistochemistry

Paraffin fixed sections (10 um) were stained with a Pan RAS antibody.

Statistical Analysis

Results of all parameters were computed employing 2 tailed student's t-test. Results are presented as means±SEM. $p<0.0.5$ was considered significant.

Results

Figure 18A:
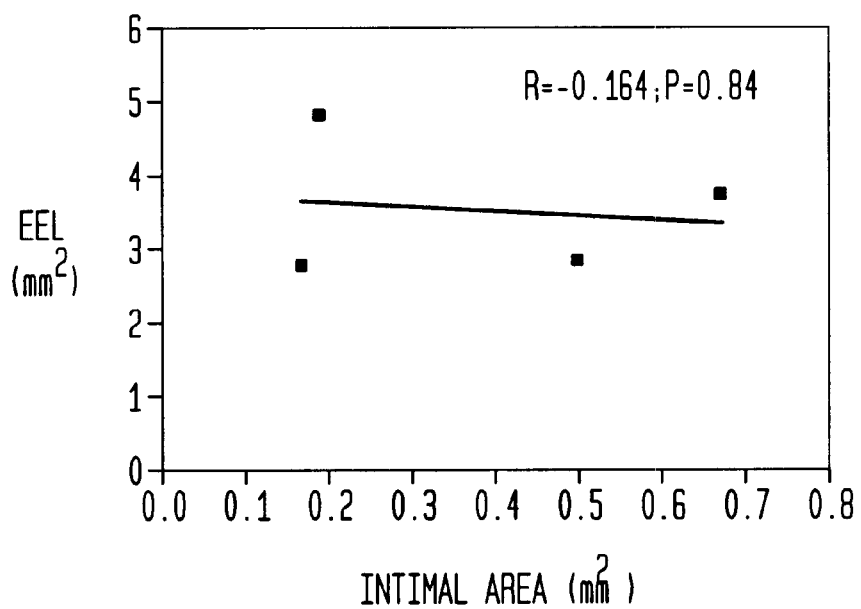
FIGS. 18A and 18B are graphs illustrating the correlation of neointimal area to external elastic laminal area as a measure of remodeling, determined in FTS (A) and control (B) treated rats.
Figure 18B:
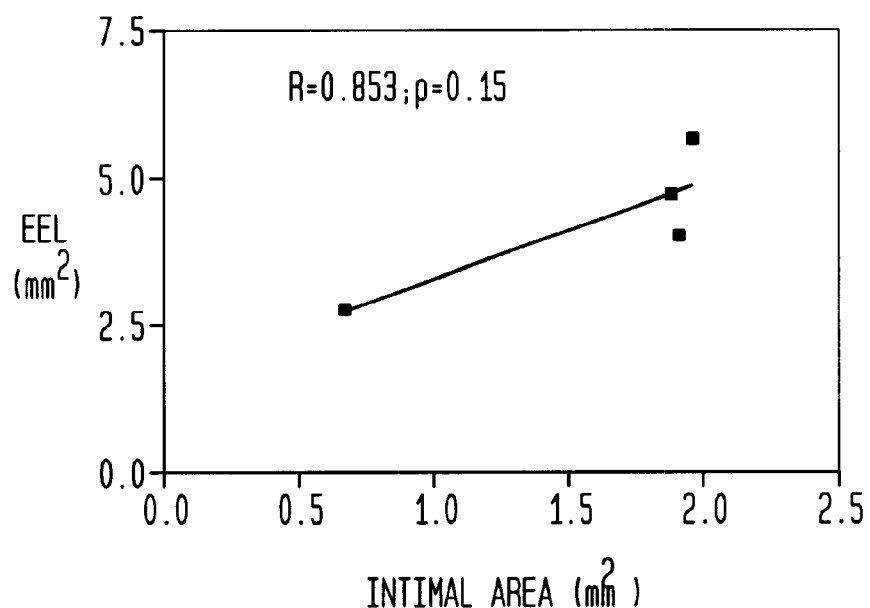

Intimal area was significantly reduced (76%) in rats treated with FTS (0.38 mm$^2$) in comparison with control treated animals (1.61 mm$^2$; p=0.02). FTS did not significantly influence medial area (0.91 mm$^2$) in the treated group as compared with the control group (1.2±0.14 mm$^2$). Intimal to medial ration was significantly reduces in FTS treated rats (0.49±0.19 mm$^2$) as compared with controls (1.29±0.20 mm$^2$; p=0.02). The luminal area was significantly increased in FTS-treated rats (1.45±0.34 mm$^2$) in comparison with control animals (2.30±32; p=01) %CSAN-N in the FTS rats was signficantly reduced (15.5±4.3%) in comparison with control treated animals (52.4±7.4%; p=0.004). As shown in FIGS. 18A and 18B, increased amount of neointimal proliferation was not associated with larger EEL area. RAS was abundantly present in the neointimal cells and only low expression was evident in the media and adventitia.

Conclusions

FTS appears as a potent inhibitor of intimal hyperplasia induced by carotid balloon injury in the rat. Increased patency of the vessel luman by FTS was mainly due to prevention of neointimal proliferation and not due to the vessel wall remodeling process. Thus, the onset of testenosis may be inhibited, or restenosis may be treated by coating or otherwise contacting the stent with the Ras antagonist prior to deployment of the stent, systemic treatment with the Ras antagonist following PTCA or administration of the Ras antagonist following heart transplantation or coronary arterial bypass graft to inhibit accelerated arteriosclerosis.

REFERENCES

1. Liu, et al., *Circulation* 79: 1374–1387 (1989).
2. Fuster, et al., *N. Engl. J. Med.* 236: 242–250 (1992).
3. Libby, et al., *Circulation* 86 (Suppl.): III47–III52 (1992).
4. Ross, *Nature* (Lond.). 362: 801–809 (1993).
5. Hanke et al., *Circulation Res.* 67: 651–659 (1990).
6. Shi, et al., *Circulation* 94: 1655–1664 (1996).
7. Andersen, *Circualation* 93: 1716–1724 (1996).
8. Ridker, et al., *Engl. J. Med.* 336: 973–733 (1997).
9. Ridker, et al., *Circualtion* 98: 731–733 (1998).
10. Koeing, *Eur. Heart J. Suppl.* 1: T19–T26 (1999).
11. Clowes, et al., *Lab Invest.* 49: 327–334 (1983).
12. Kaltenbach, et al., *Eur. Heart J.* 6: 276–281 (1995).
13. Nobuyoshi, et al., *J. Am. Coll. Cardiol.* 12: 616–623 (1988).
14. RITA Trial Participants (1993) Coronary angioplasty versus coronary artery bypass surgery: the Randomised Intervention Treatment of Angina (RITA) trial. *Lancet.* 341: 573–580.
15. Califf, et al., *J. Am. Coll. Cardiol.* 17: 2B–13B (1991).
16. Popma, et al. *Circulation* 84: 1426–1436 (1991).
17. Franklin, et al., *Coronary Artery Dis.* 4: 232–242 (1993).
18. Teirstein, et al., *N. Eng. J. Med* 336: 1697–1703 (1997).
19. Condado, et al., *Circulation* 96: 727–732 (1997).

EXAMPLE 7

Synthesis of Various FTS Analogs

Materials: Methylthiosalicylate (cat #35,775-8),
2-amino-5-chlorobenzoic acid (cat #37,80406),
2-amino-4-chlorobenzoic acid (cat #A4,546-7), and
2-amino-5-fluorobenzoic acid (cat #36798-2)—were obtained from Aldrich.

Synthesis 4-chlorothiosalicylic acid, 5-chlorothiosalicylic acid and 5-fluorothiosalicylic acid were prepared by general procedures as detailed previously (Katz, et al., JOC 18:1380–1402 (1953); Allen, C. F. H. and McKay, Org. Synthesis 11:580; Org. Synthesis IV:295; Okachi, et al., J. Med Chem. 28:1772–1779 (1985); Carmelin, et al., J. Med. Chem 29:743–751 (1994); Tarbell, et al., Am. Soc. 74:48 (1952); Org. React. 5:193–228 (1949).

Synthesis of 5-Chlorothiosalicylic and 4-Chlorothiosalicylic Acid

A mixture of crystallized sodium sulfide (39 g, 0.17 moles) and powdered sulfur (5.1 g) was dissolved by heating and stirring in 43.5 cc of boiled water. A solution of 40 g sodium hydroxide in 15 cc water was then added and the mixture was cooled stepwise, first in cold water, then by a freezing mixture of ice and salt. 75 cc of water, 25 g (0.15 mole) of 5-chloroanthranilic or of 4-chloroanthranilic acid and 30 cc of concentrated hydrochloric acid were added to a separate beaker which was set by a freezing mixture to 0° C. The mixture was stirred and cooled to about 6° C. Meanwhile, 10.35 g (0.15 mole) of sodium nitrite were dissolved in 42 cc of hot water and the solution was cooled on ice. When the temperature dropped to 5° C. the nitrite solution was run through a separatory funnel into the anthranilic solution. About 75 g of cracked ice were added at a rate that kept temperature below 5° C. The diazo solution was then added to the alkaline sulfide solution (which was kept at a temperature of 2–4° C.) along with 150 g of ice and temperature was kept below 5° C. The mixture was allowed to warm up to room temperature, and when evolution of nitrogen ceased (about 2 h), concentrated hydrochloric acid (27 cc) were added until the solution was acidic to Congo red paper. The precipitate of disulfide was filtered and washed with water.

To remove the excess sulfur the precipitate was dissolved by boiling with a solution of 9 g of anhydrous sodium carbonate in 300 cc of water and the mixture was filtered while hot. The solution was then acidified with hydrochloric acid, the precipitate was filtered and the cake was sucked to dryness. The cake was dried further by addition of toluene followed by azeothropic evaporation. This procedure was repeated twice. The cake was mixed with 4.05 g of zinc dust and 45 cc of glacial acetic acid, and the mixture was refluxed for overnight. The mixture was cooled and filtered with suction. The filter cake was washed once with water and transferred to a 150 cc beaker. The cake was suspended in 30 cc of water and the suspension was heated to boiling. The hot solution was made strongly alkaline by the addition of about 6 cc of a 33% sodium hydroxide solution. The alkaline solution was boiled for about 20 min. and the insoluble material was filtered. The product was then precipitated by the addition of concentrated hydrochloric acid to make the solution acid to Congo red paper. The product was filtered, washed once with water, and dried in an oven at 100–130° C. (5-chlorothiosalicylic acid, mp 162° C.).

Synthesis of 5-Fluorothiosalicylic Acid

A mixture of crystallized sodium sulfide (1.8 g, 0.01 mole) and powdered sulfur (0.24 g) was dissolved by heating and stirring in 2 cc of boiled water. A solution of 0.3 g of sodium hydroxide in 1 cc of water was then added and the mixture was cooled stepwise as detailed above. Four cc of water, 1 g (0.007 mole) of 5-fluoro-anthranilic acid and 1.4 cc of concentrated hydrochloric acid were added to a separate beaker which was set by a freezing mixture to 0° C. The mixture was stirred and cooled to about 6° C. Meanwhile, 0.48 g (0.007 mole) of sodium nitrite were dissolved in 2 cc of hot water and the solution was cooled on ice. When the temperature dropped to 5° C., the nitrite solution was run through a separatory funnel into the anthranilic solution. About 3.5 g of cracked ice were added at a rate that kept temperature below 5° C. The diazo solution was then added to the alkaline sulfide solution (which was kept at a temperature of 2°–4° C.) along with 10 g of ice and temperature was kept below 5° C. The mixture was allowed to warm up to room temperature, and when evolution of nitrogen ceased (about 2 h), concentrated hydrochloric acid (~1.5 cc) was added until the solution was acid to Congo red paper. The precipitate of disulfide was filtered and washed with water. To remove the excess sulfur, the precipitate was dissolved by boiling with a solution of 0.5 g of anhydrous sodium carbonate in 15 cc of water and the mixture was filtered while hot. The solution was then acidified with hydrochloric acid, the precipitate was filtered and the cake was sucked to dryness. The cake was dried by addition of toluene followed by azeothropic evaporation. This procedure was repeated twice. The cake was mixed with 0.2 g of zinc dust and 2 cc of glacial acetic acid, and the mixture was refluxed for overnight. The mixture was cooled and filtered with suction. The filter cake was washed once with water and transferred to a 10 cc beaker. The cake was suspended in 2 cc of water and the suspension was heated to boiling. The hot solution was made strongly alkaline by the addition of about 0.3 cc of a 33% sodium hydroxide solution. The alkaline solution was boiled about 20 min. and the insoluble material was filtered. The product was then precipitated by the addition of concentrated hydrochloric acid to make the solution acid to Congo red paper. The product was filtered with suction, washed once with water, and dried in an oven at 100°–130° C.; mp was 185° C.

Synthesis of 5-Chloro-FTS 5-chloro-thiosalicylic acid (1.9 g, 12 mmol), guanidine carbonate (2.6 g, 14.0 mmol), and trans, trans-farnesylbromide (3.4 g, 12 mmol) in 150 ml of acetone were mixed overnight at room temperature. After the acetone had evaporated, chloroform was added together with a few drops of 2N HCl. The mixture was washed with water and the organic phase was separated, dried on magnesium sulfate and then evaporated. A yellowish powder was obtained. The product, 5-Cl-FTS, was purified on silica gel with ethyl acetate and mixtures of chloroform and ethyl acetate as eluants (13% yield). 5-Cl-FTS: IUPAC name: 5-chloro-2-(3,7,11-trimethyl-dodeca-2,6,10-trienyl sulfanyl)-benzoic acid.

Appearance pale yellowish oil; TLC (silica gel, chloroform ethyl acetate 1:1) Rf=0.70; HRMS m/e 394,392[M+] ($C_{22}H_{29}O_2SCl$); $^1$H-NMR ($CDCl_3$, TMS) δ 1.6 (bs 1.65(s, 3H), 2.1(m, 8H), 3.6(d, 2H), 5.1(m, 2H), 5.3(bt, 1H), 7.2(m, 1H, Arom), 7.4(m, 1H, Arom), 7.9(m, 1H, Arom) ppm.

Synthesis of 4-Chloro-FTS 4-chloro-thiosalicylic acid (0.9 g, 5 mmol), guanidine carbonate (1.3 g, 7 mmol), and trans, trans-farnesylbromide (1.4 g, 5 mmol) in 75 ml of acetone were mixed overnight at room temperature. After the acetone had evaporated, chloroform was added together with a few drops of 2N HCl. The mixture was washed with water and the organic phase was separated, dried on magnesium sulfate and then evaporated. A yellowish oil was obtained. The product, 4-Cl-FTS, was purified on silica gel with mixtures of chloroform and hexane (19:1 to 100% chloroform) as eluants (17.8% yield). 4-Cl-FTS: IUPAC name: 4-chloro-2-(3,7,11-trimethyl-dodeca-2,6,10-trienyl sulfanyl)-benzoic acid.

Appearance pale, yellow oil; TLC (silica gel, chloroform ethyl acetate 1:1) Rf=0.66; HRMS m/e 394,392[M+] ($C_{22}H_{29}O_2SCl$); $^1$H-NMR ($CDCl_3$, TMS) δ 1.6 (s, 6H), 1.74(d, 6H), 2.1(m, 8H), 3.6(d, 2H), 5.1(bt, 2H), 5.3(bt, 1H), 7.16(m, 1H, Arom), 7.29(m, 1H, Arom), 8.06(m, 1H, Arom) ppm.

Synthesis of 5-Fluoro-FTS 5-fluoro-thiosalicylic acid (0.31 g, 2 mmol), guanidine carbonate (0.46 g, 2.4 mmol), and trans, trans-farnesylbromide (0.61 g, 2.15 mmol) in 25 ml of acetone were mixed overnight at room temperature. After the acetone had evaporated, chloroform was added together with a few drops of 2N HCl. The mixture was washed with water and the organic phase was separated, dried on magnesium sulfate and then evaporated. A yellow solid was obtained. The product, 5-F-FTS, was purified on silica gel with mixtures of chloroform and ethyl acetate (5:1-1:5) as eluants (18% yield). 5-F-FTS: IUPAC name: 4-fluoro-2-(3,7,11-trimethyl-dodeca-2,6,10-trienyl sulfanyl)-benzoic acid.

Appearance yellow solid; TLC (silica gel, chloroform ethyl acetate 1:1) Rf=0.71; HRMS m/e 376[M+] ($C_{22}H_{29}O_2SCl$); $^1$H-NMR (CDCl$_3$) δ 1.6 (s, 6H), 1.7(d, 6H), 2.1(m, 8H), 3.6(d, 2H), 5.1(m, 2H), 5.3(bt, 1H), 7.3(m, 1H, Arom), 7.43(m, 1H, Arom), 8.1(m, 1H, Arom) ppm.

Synthesis of S-Farnesyl-methylthiosalicylic Acid (FMTS)

Methylthiosalicylic acid (0.3 g, 1.76 mmol), guanidine carbonate (0.38 g, 2.0 mmol), and trans,trans-farnesylbromide (0.5 g, 1.76 mmol) in 22 ml of acetone were mixed overnight at room temperature. After the acetone had evaporated, hexane was added and the precipitated product was filtered with suction (14% yield). FMTS: WPAC name: methyl-2-(3,7,11-trimethyl-dodeca-2,6,10-trienyl sulfanyl)-benzoate.

Appearance yellow brown paste; TLC (silica gel, chloroform pentane 1:1) Rf=0.71; ERMS m/e 372[M+] ($c_{23}H_{32}O_2S$); $^1$H-NMR (CDCl$_3$) δ 1.6 (s, 6H), 1.65(d, 6H), 2.1(m, 8H), 3.47(s, 3H), 3.6(d, 2H) 5.1(bt, 2H), 5.35(bt, 1H), 7.2(m, 1H, Arom), 7.35(m, 1H, Arom), 7.45(m, 1H, Arom), 8.15(m, 1H, Arom) ppm.

All patent and non-patent publications cited in this specification are indicative of the level of skill of those skilled in the art to which this invention pertains. All these publications are herein incorporated by reference to the same extent as if each individual publication or patent application were specificaly and individually indicated to be incorporated by reference.

Various modifications of the invention described herein will become apparent to those skilled in the art. Such modifications are intended to fall within the scope of the appending claims.

What is claimed is:

1. A method of inhibiting Ras-induced proliferation of cells associated with a non-malignant disease or pathological state, comprising: administering to a patient a Ras antagonist in an amount effective to inhibit the proliferation, wherein said ras antagonist is represented by the formula

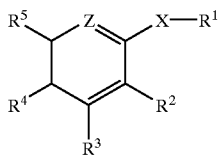

wherein $R^1$ represents farnesyl, geranyl or geranyl-geranyl;

Z represents C—$R^6$ or N;

$R^2$ represents H, CN, the groups COOR$^7$, SO$_3$R$^7$, CONR$^7$R$^8$, COOM, SO$_3$M and SO$_2$NR$^7$R$^8$, wherein R$^7$ and R$^8$ are each independently hydrogen, alkyl or alkenyl, and wherein M is a cation;

$R^3$, $R^4$, $R^5$ and $R^6$ are each independently hydrogen, carboxyl, alkyl, alkenyl, aminoalkyl, nitroalkyl, nitro, halo, amino, mono- or di-alkylamino, mercapto, mercaptoalkyl, axido, or thiocyanato;

X represents O, S, SO, SO$_2$, NH or Se; and the quaternary ammonium salts and N-oxides of the compounds of said formula when Z is N.

2. The method of claim 1 wherein the patient is afflicted with an autoimmune disease characterized by a proliferation of T-cells.

3. The method of claim 2 wherein the autoimmune disease is systemic lupus erythmatosus.

4. The method of claim 2 wherein the autoimmune disease is multiple sclerosis.

5. The method of claim 2 wherein the autoimmune disease is secondary antiphospholipid syndrome.

6. The method of claim 1 wherein the patient is afflicted with cirrhosis.

7. The method of claim 1 wherein said Ras antagonist is farnesylthiosalicyclic acid (FTS).

8. The method of claim 1 wherein the Ras antagonist is 2-chloro-5-farnesylaminobenzoic acid (NFCB).

9. The method of claim 1 wherein the Ras antagonist is farnesyl thionicoatinic acid (FTN).

10. The method of claim 1 wherein the Ras antagonist is 5-fluoro-FTS.

11. The method of claim 1 wherein the Ras antagonist is 5-chloro-FTS.

12. The method of claim 1 wherein the Ras antagonist is 4-chloro-FTS.

13. The method of claim 1 wherein the Ras antagonist is 5-farnesylmethylthiosalicylic acid.

14. The method of claim 1 wherein said Ras antagonist is administered parenterally.

15. The method of claim 1 wherein said Ras antagonist is administered orally in a formulation containing cyclodextrin.

16. A method of inhibiting Ras-induced proliferation of cells associated with a non-malignant disease or pathological state, comprising contacting the cells with a Ras antagonist in an amount effective to inhibit the proliferation, wherein the Ras antagonist is represented by the formula

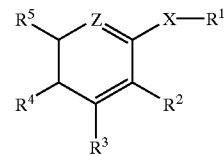

wherein $R^1$ represents farnesyl, geranyl or geranyl-geranyl;

Z represents C—$R^6$ or N;

$R^2$ represents H, CN, the groups COOR$^7$, SO$_3$R$^7$, CONR$^7$R$^8$, COOM, SO$_3$M and SO$_2$NR$^7$R$^8$, wherein R$^7$ and R$^8$ are each independently hydrogen, alkyl or alkenyl, and wherein M is a cation;

$R^3$, $R^4$, $R^5$ and $R^6$ are each independently hydrogen, carboxyl, alkyl, alkenyl, aminoalkyl, nitroalkyl, nitro, halo, amino, mono- or di-alkylamino, mercapto, mercaptoalkyl, axido, or thiocyanato;

X represents O, S, SO, SO$_2$, NH or Se; and the quaternary ammonium salts and N-oxides of the compounds of said formula when Z is N.

17. The method of claim 2 wherein the autoimmune disease is rheumatoid arthritis.

18. The method of claim 2 wherein the autoimmune disease is graft rejection.

19. The method of claim 2 wherein the autoimmune disease is psoriasis.

20. The method of claim 2 wherein the autoimmune disease is type-1 diabetes.

21. The method of claim 1 wherein the Ras antagonist is administered topically.

22. The method of claim 21 wherein the Ras antagonist is administered by way of a transdermal patch.

* * * * *

UNITED STATES PATENT AND TRADEMARK OFFICE
CERTIFICATE OF CORRECTION

PATENT NO.    : 6,462,086 B1
DATED         : October 8, 2002
INVENTOR(S)   : Yoel Kloog et al.

It is certified that error appears in the above-identified patent and that said Letters Patent is hereby corrected as shown below:

<u>Title page,</u>
Item [75], Inventors, "Jerusalem" should read -- Malcha --.

<u>Column 1,</u>
Line 42, delete the comma after "subtypes".
Line 67, "emphasized" should read -- emphasizes --.

<u>Column 2,</u>
Line 63, delete "and" after "angioplasty".

<u>Column 3,</u>
Line 49, insert -- Experimental Allergic Encephalomyelitis -- after "acute".

<u>Column 4,</u>
Line 2, "reated" should read -- treated --.
Line 5, insert -- Experimental Autoimmune Neuritis -- before "EAN".
Line 6, "0-3-" should read -- 0-30 --.
Line 32, insert -- saline treated (filled hatch bars) and FTS treated (filled bars) -- after "the" and delete "(filled-hatched bars)".

<u>Column 6,</u>
Line 5, "MAPR" should read -- MAPK --.
Lines 11 and 12, delete "hormone/growth factor" and insert -- for t-cell antigens, hormones and growth factors -- after "receptors".
Line 12, "result" should read -- results --.
Line 23, "ras" should read -- Ras --.

<u>Column 8,</u>
Line 27, "memberances" should read -- membranes --.
Line 34, "gallates" should read -- gallate --.

<u>Column 10,</u>
Line 8, "mater" should read -- matter --.
Lines 14 and 16, "downregulation" should read -- down-regulation --.
Line 63, "*Tuberculosis*" should read -- *tuberculosis* --.

<u>Column 11,</u>
Line 19, "*Tuberculosis*" should read -- *tuberculosis* --.

UNITED STATES PATENT AND TRADEMARK OFFICE
CERTIFICATE OF CORRECTION

PATENT NO. : 6,462,086 B1
DATED : October 8, 2002
INVENTOR(S) : Yoel Kloog et al.

It is certified that error appears in the above-identified patent and that said Letters Patent is hereby corrected as shown below:

Column 14,
Line 29, "in-vivo" should read -- *in vivo* --.
Line 47, ":" should read -- -- --.

Column 17,
Line 56, insert -- of Ras -- after "Inhibition".
Line 59, insert -- The results show that FTS lowered the concentration of Ras in membranes of spleenocytes both *in vivo* and *in vitro*. -- after "mice."
Line 63, "below" should read -- above --.

Column 18,
Lind 52, insert -- in the control group -- after "4.12±0.61".

Column 23,
Line 57, "sield" should read -- field --.

Column 27,
Line 34, "anti fibrotic" should read -- anti-fibrotic --.

Column 31,
Line 1, insert -- inhibited -- after "µM)".

Column 32,
Line 63, "Artherosclerosis" should read -- Atherosclerosis --.
Line 66, insert -- hyperplasia -- after "neointimal".

Column 33,
Line 4, "artherosclerosis" should read -- atherosclerosis --.
Line 49, insert -- hyperplasia -- after "neointimal".
Line 50, insert -- ) -- after "size".
Line 56, "RAS" should read -- Ras --.
Line 67, "ration" should read -- ratio --.
Line 67, "reduces" should read -- reduced --.

Column 34,
Line 7, insert -- the -- before "increased".
Line 8, "RAS" should read -- Ras --.
Line 8, insert -- Immunostainable -- before "Ras".
Line 60, insert -- The compounds -- before "4-chlorothiosalicylic".

UNITED STATES PATENT AND TRADEMARK OFFICE
CERTIFICATE OF CORRECTION

PATENT NO. : 6,462,086 B1
DATED : October 8, 2002
INVENTOR(S) : Yoel Kloog et al.

It is certified that error appears in the above-identified patent and that said Letters Patent is hereby corrected as shown below:

<u>Column 35,</u>
Line 1, "Chlorothiosalicylic" should read -- chlorothiosalicylic -- in both occurrences.
Line 48, "Fluorothiosalicylic" should read -- fluorothiosalicylic --.

<u>Column 36,</u>
Line 44, "Chloro-FTS" should read -- chloro-FTS --.
Line 45, insert -- The compounds -- before "4-chloro-thiosalicylic".
Line 63, "5-Fluoro-FTS" should read -- 5-fluoro-FTS --.

<u>Column 37,</u>
Line 13, "S-Farnesyl-methylthiosalicyic" should read
-- S-farnesyl-methylthiosalicyic --.

<u>Column 38,</u>
Line 21, "5-farnesylmethylthiosalicylic" should read
-- S-farnesylmethylthiosalicylic --.

Signed and Sealed this

Eighth Day of April, 2003

JAMES E. ROGAN
*Director of the United States Patent and Trademark Office*